United States Patent
Matsumoto et al.

(10) Patent No.: US 6,808,689 B1
(45) Date of Patent: Oct. 26, 2004

(54) REACTOR FOR CATALYTIC GAS PHASE OXIDATION

(75) Inventors: Yukihiro Matsumoto, Kobe (JP);
Masakatsu Mori, Hyogo (JP);
Masatsuga Kitaura, Himeji (JP);
Osamu Dodo, Hyogo (JP); Michio Tanimoto, Himeji (JP)

(73) Assignee: Nippon Shokubai Co., LTD, Osaka (JP)

( * ) Notice: Subject to any disclaimer, the term of this patent is extended or adjusted under 35 U.S.C. 154(b) by 804 days.

(21) Appl. No.: 09/652,209

(22) Filed: Aug. 30, 2000

(30) Foreign Application Priority Data

Aug. 31, 1999 (JP) ............................................. 11-246057
Aug. 31, 1999 (JP) ............................................. 11-246058

(51) Int. Cl.[7] ................. B01J 8/04; F28D 7/00
(52) U.S. Cl. .............. 422/196; 422/197; 422/201; 422/202; 422/205; 422/211; 422/312; 165/81; 165/140; 165/161; 165/162; 165/201
(58) Field of Search ................. 422/196, 197, 422/201, 202, 205, 211, 312; 165/81, 140, 161, 162, 201

(56) References Cited

U.S. PATENT DOCUMENTS

| | | | | |
|---|---|---|---|---|
| 3,871,445 A | * | 3/1975 | Wanka et al. | 165/104.14 |
| 4,203,906 A | * | 5/1980 | Takada et al. | 549/248 |
| 4,256,783 A | * | 3/1981 | Takada et al. | 422/197 |
| 5,149,884 A | * | 9/1992 | Brenner et al. | 568/471 |
| 5,277,247 A | * | 1/1994 | Cameron | 165/159 |
| 5,821,390 A | | 10/1998 | Ruppel et al. | |

FOREIGN PATENT DOCUMENTS

| | | |
|---|---|---|
| GB | A1-004234 | 9/1965 |
| GB | 2 007 523 A | 5/1979 |

* cited by examiner

*Primary Examiner*—Glenn Caldarola
*Assistant Examiner*—Alexis Wachtel
(74) *Attorney, Agent, or Firm*—Mathews, Collins Shepherd & McKay, PA

(57) ABSTRACT

The temperature distribution of a heating medium in the reactor is allayed and the occurrence of hot spots is repressed. In a shell-and-tube type reactor provided with donut type and disc type baffle plates, reaction tubes are disposed even in the holes formed in the donut type baffle plates and an empty space devoid of a configuration of the reaction tubes is formed at the center of the shell. According to this invention, (meth)acrylic acid and/or (meth)acrolein can be produced at a low energy by catalytic gas phase oxidation of propylene- or isobutylene-containing gas.

18 Claims, 13 Drawing Sheets

REACTOR FOR CATALYTIC GAS PHASE OXIDATION

BACKGROUND OF THE INVENTION

1. Field of the Invention

This invention relates to a shell-and-tube type reactor provided with reaction tubes not supported by a donut type baffle plate, a method for the production of (meth)acrylic acid or (meth)acrolein using the reactor; a shell-and-tube type reactor furnished with a plurality of built-in reaction tubes and provided with a baffle plate capable of varying the moving direction of a heating medium introduced into the shell thereof, and a method for the production of (meth) acrylic acid and/or (meth)acrolein using the reactor.

2. Description of the Related Art

The reaction of catalytic gas phase oxidation using a shell-and-tube type reactor is a means generally used for the purpose of efficiently removing the heat generated by the reaction. By the use of shell-and-tube type reactors provided in the shell of the reactor with a plurality of built-in reaction tubes, the raw material gas for the reaction is supplied to the reaction tubes packed with a catalyst to effect the reaction of catalytic gas phase oxidation and the heating medium capable of removing the reaction heat is circulated in the shell thereof to remove the generated heat of reaction.

The reaction of catalytic gas phase oxidation using the shell-and-tube type reactor tends to give rise to a hot spot on the raw material inlet side and poses problems such as deteriorating the catalyst by an excessive exothermic reaction and degrading selectivity to the subject product.

U.S. Pat. No. 3,871,445, for example, discloses a shell-and-tube type reactor provided with a circulation device for a heating medium and further furnished in the shell with baffle plates, in order to solve these problems. It has a mention that, owing to the presence of such baffle plates, the velocity of lateral flow within one area is retained substantially constant and the heat transfer within the area is then fixed. To be specific, the reactor illustrated in the paper has built therein upright reaction tubes arranged in an annular pattern, has the upper and lower ends of the reaction tubes fitted as tightly sealed to the tube sheets, and has a plurality of donut type and disc type baffle plates horizontally and alternately spaced and attached laterally to the reaction tubes so as to form passage sections centrally and externally. The shell is provided at the center thereof with a tie rod and spacer to fix the disc type baffle plates.

The conventional shell-and-tube type reactor which has donut type and disc type baffle plates built therein is schematically illustrated in FIG. 1. Generally, at the center of a shell 1, a tie rod and spacer 7 are disposed to connect the disc type baffle plate 3. The donut type plates 2 are connected through another tie rod and spacer. Reaction tubes 4 are disposed through holes formed in the baffle plates and built in the shell 1. A heating medium 10 is introduced via an annular conduit 11a into the shell 1, for example, using an axial-flow pump not shown. The heating medium 10 so introduced is moved in the shell 1 while changing the flow direction by the donut type baffle plate 2 and disc type baffle plate 3. The transfer of the heating medium 10 is intended to remove the reaction heat from the reaction tubes, and the baffle plates are required for the purpose of securing a passage for the heating medium 10 and enabling the reaction tubes to be uniformly removed of heat. In this case, the reaction tubes 4 are fully supported by the donut type baffle plate 2 without fail. If they are not fully supported, the central hole of the donut type baffle plate 2 is suffered to impart a vertical flow to the heating medium 10 and then the reaction tubes 4 are prevented from sufficiently removing the heat uniformly. The prominence of lateral transfer of the heating medium forces an additional pressure drop of heating medium and calls for an unduly large energy for the power.

The heating medium introduced into the shell is expelled out of the shell after it has been served for the purpose of removing the reaction heat from the tubes, then cooled by a heat exchanger etc, and circulated to the shell to reuse therein. U.S. Pat. No. 5,821,390, for example, discloses a method for effecting catalytic gas phase oxidation of propene into acrolein while maintaining specific selectivity and conversion using a shell-and-tube type reactor, introducing a heating medium in co-current flow, utilizing baffle plates disposed in the reactor, and adjusting the flow rate of the heating medium so that the temperature rise of the heating medium in the reactor falls in the range of 2–10° C. This official gazette discloses that the catalytic gas phase oxidation of propene into acrolein is attained using a catalytically active complex metal oxide warmed in the shell-and-tube reactor while reducing the hot spot temperature.

The heat yield is calculated by the balance between the amount of heat generated by the reaction and the amount of heat consumed by cooling. Even when the heating medium is introduced into the shell for the purpose of removing the reaction heat, the failure of removal of the reaction heat uniformly throughout the whole of reaction tubes undeniably entails the possibility that the reaction tubes will suffer an undue temperature rise, increase side reactions, lower the yield of reaction, accelerate deterioration of the catalyst, and induce a run-away reaction. It is clear from the example cited in U.S. Pat. No. 5,821,390 that under the conditions which fix the quantity of heat to be generated, the pump power required to limit the rise of temperature of the heating medium to 1° C. is completely identical even if the heating medium is passed in counter or co-current flow within the shell. As a result, the desirability of developing an efficient means capable of uniformly reducing the hot spot temperature in each of the reaction tubes has been finding growing recognition.

Further, there is a time when the heating medium is introduced into the shell, a gas is entrained to introduce into the shell. Since the heating medium receives a large temperature variation as by being heated in consequence of the removal of the reaction heat from the reaction tubes and being subsequently cooled, it tends to include a gas therein with expansion and contraction and this gas eventually collects in the shell. Generally, when the heating medium is introduced into the shell at the start of use of the reactor, an air vent is opened to facilitate the introduction of the heating medium. The air vent is normally kept in a closed state while the reactor is in use. Hence, the gas forms a pool in the upper part of the shell. Since the heating medium is absent from the pool of this gas, the relevant part of the reactor cannot be sufficiently removed in heat. There are times when the reaction tubes may be corroded by the gas.

Thus, the conventional shell-and-tube type reactor relies on the disposition of baffle plates and the cyclic use of the heating medium at a specific flow rate to remove the reaction heat from reaction tubes. This heat removal from the reaction tubes is not called sufficient. When the desired product is manufactured on a commercial scale using this shell-and-tube type reactor, the harmonization between the yield of the product and the power to be consumed constitutes itself an important issue. In particular, an increase in the amount of the heating medium circulated for the purpose of efficiently removing the heat using the shell-and-tube type reactor brings the disadvantage of eventually increasing the power energy for circulating the heating medium. An attempt to enlarge the heat transfer area by decreasing the tube diameter increases the number of reaction tubes and the cost of the reaction apparatus.

Consequently, the development of a reactor capable of uniformly removing reaction heats, reducing hot spot temperatures, maintaining or enhancing the selectivity of the desired product, and decreasing the power energy has been desired.

SUMMARY OF THE INVENTION

We have investigated the movement of a heating medium in the reactor and have then discovered that when reaction tubes are disposed on inner sides of donut type baffle plates, the reactor can be miniaturized and the desired product can be obtained in the same yield as in the conventional reactor. This invention has been achieved as a result.

An object of this invention is to provide a reactor for the gas phase oxidation.

Another object of this invention is to provide a method for the production of (meth)acrylic acid and/or (meth)acrolein using the reactor mentioned above.

Further object of this invention is to provide uses for the reactor mentioned above.

The object of this invention is accomplished by a shell-and-tube type reactor provided with a cylindrical shell having disposed on the outer periphery thereof a plurality of annular conduits for guiding a heating medium in or out in the radial direction and having a raw material inlet and product outlet; a circulation device for mutually connecting the plurality of annular conduits; lots of reaction tubes kept by a plurality of tube sheets; and donut type and disc type baffle plates disposed in the longitudinal direction of the tubes and adapted to vary the direction of the heating medium introduced into the reactor shell; and characterized in that the reaction tubes are kept at center distances 1.2–1.4 times the outside diameter thereof; the shell has at the center thereof an empty space devoid of arrangement of the reaction tubes; and the donut type baffle plates avoid supporting part of the reaction tubes.

The object of this invention is further accomplished by a method for the production of (meth)acrylic acid and/or (meth)acrolein using the reactor mentioned above.

The object of this invention is also accomplished by a method for using the reactor mentioned above for the production of (meth)acrylic acid and/or (meth)acrolein.

According to this invention, by disposing such reaction tubes as are not supported by the areas of donut type baffle plates, it is possible to decrease the electric power of a pump. Moreover, this decrease of the electric power is attained without varying the selectivity and yield of the desired product.

The present reactor is particularly suitable for the production of (meth)acrylic acid and/or (meth)acrolein because the use of this reactor can repress the deviation of the temperature distribution of heating medium.

The above and other objects, features and advantages of the present invention will become clear from the following description of the preferred embodiments.

DETAILED DESCRIPTION OF THE PREFERRED EMBODIMENTS

Figure 1:
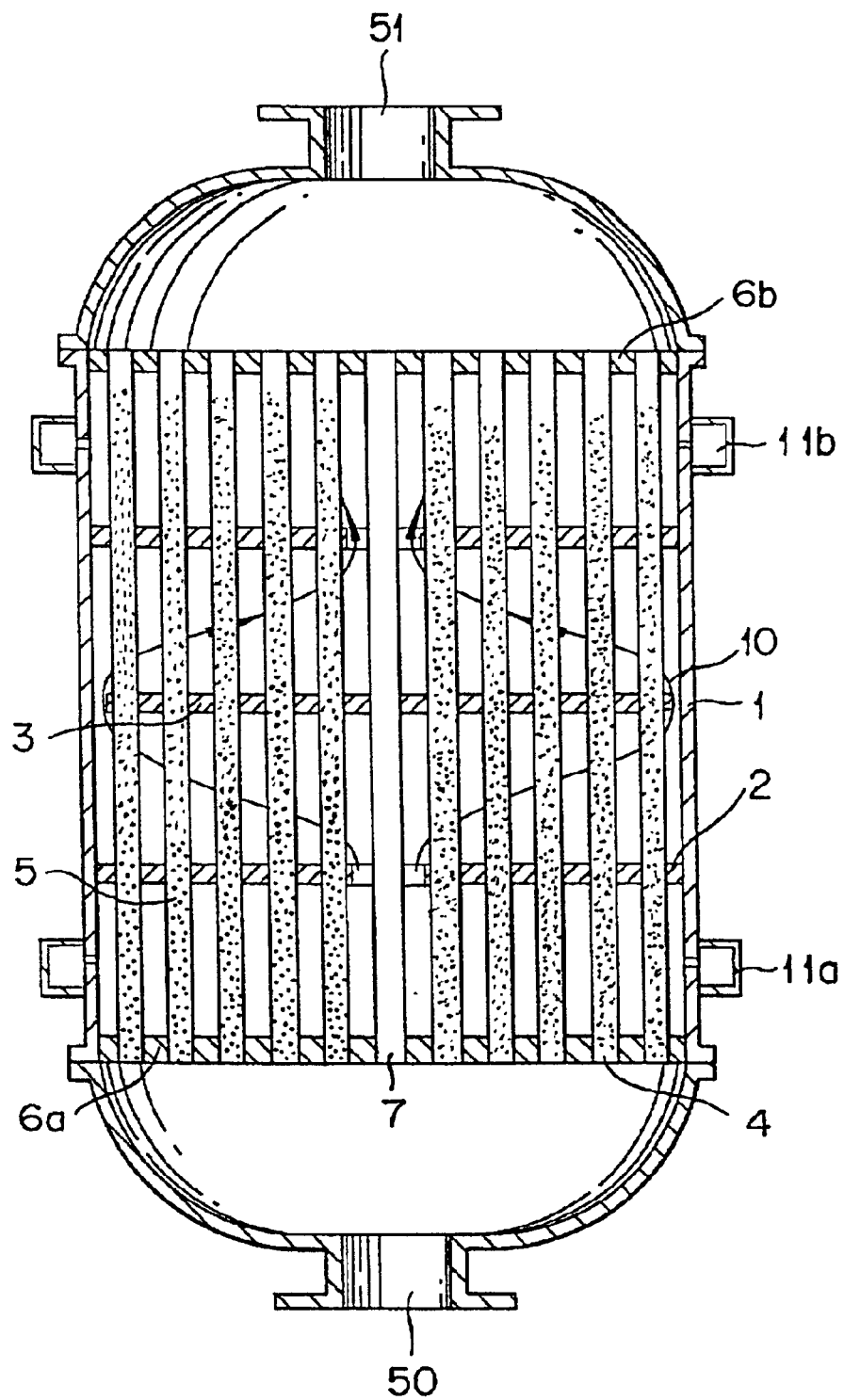
FIG. 1 is an explanatory cross sectional diagram for schematically illustrating a conventional shell-and-tube type reactor.

This invention will be explained below as divided into (I) means for having reaction tubes also in hole parts of donut type baffle plates and providing at the center of the shell an empty space having no reaction tube disposed and (II) means for providing a circulation passage for a heating medium.

(I) Means for Having Reaction Tubes Also in Hole Parts of Donut Type Baffle Plates and Providing at the Center of the Shell an Empty Space Having no Reaction Tube Disposed This invention concerns a shell-and-tube type reactor provided with a cylindrical shell having disposed on the outer periphery thereof a plurality of annular conduits for guiding a heating medium in or out in the radial direction and having a raw material inlet and product outlet; a circulation device for mutually connecting the plurality of annular conduits; lots of reaction tubes kept by a plurality of tube sheets; and donut type and disc type baffle plates disposed in the longitudinal direction of the reaction tubes and adapted to vary the direction of the heating medium introduced into the shell; and characterized in that the reaction tubes are kept at center distances 1.2–1.4 times the outside diameter thereof; the shell has at the center thereof an empty space devoid of arrangement of the reaction tubes; and the donut type baffle plates avoid supporting part of the reaction tubes.

Conventionally, baffle plates have been intended to secure a passage for a heating medium. Since they give rise to a vertical flow and degrade thermal efficiency when they are not fully supported, the whole reaction tubes are fully supported by donut type baffle plates. When disposing the reaction tubes partly inside the donut type baffle plates, it has been demonstrated that they decrease the power energy for producing the flow of the heating medium and reduce the cross sectional area of the reactor relative to the reaction tubes accommodated therein as well while retaining the yield and selectivity of the desired product. Now, the mode of this invention will be described with reference to FIG. 2.

This invention concerns a shell-and-tube type reactor provided with a cylindrical reactor shell 201 having disposed on the outer periphery thereof a plurality of annular conduits 211a, 211b for guiding a heating medium in or out in the radial direction and having a raw material inlet 250 and a product outlet 251; a plurality of reaction tubes 204 constrained by two tube sheets 206a, 206b for partitioning the raw material inlet 250 and the product outlet 251 of the reactor shell 201; and donut type baffle plates 202 and disc type baffle plates 203 adapted to vary the direction of the heating medium introduced into the reactor shell 201 and disposed in the longitudinal direction of the reaction tubes.

The donut type baffle plates 202 and the disc type baffle plates 203 are alternately disposed in the longitudinal direction of the reaction tubes 204. The distances between the donut type baffle plates 202 and the disc type baffle plates 203 are not particularly restricted. When the hot spots of reaction tubes vary with the reaction of catalytic gas phase oxidation, the distance may be suitably chosen, depending on the positions and temperature changes of the hot spots.

The reaction tubes 204 are required to dispose at center distances 1.2–1.4 times, preferably 1.25–1.35 times, and particularly preferably 1.25–1.30 times, the outside diameter of the reaction tube. If the center distances are less than 1.2 times, the distances between the reaction tubes will be narrowed to the extent of lowering the thermal removal efficiency in those reaction tubes which fall in the near center of the shell notwithstanding the decreased distances are useful for the miniaturization of the reactor, and then making the reduction of hot spot temperature difficult. Conversely, if the center distances exceed 1.4 times, the excess will be at a disadvantage in enlarging the reactor, lowering the linear velocity of fluid in the shell, channelling the stream of heating medium, and lowering the efficiency of heat removal. The inside and outside diameters and length of the reaction tubes are not particularly restricted. Sizes of the reaction tubes used in the known reaction for catalytic gas phase oxidation can be chosen. In this invention, the reaction tubes commendably have an inside diameter in the range of 15–50 mm, preferably 20–40 mm, and particularly preferably 20–30 mm.

Further, this invention is characterized in that the shell is provided in the central part thereof with an empty space, and reaction tubes 204a are not supported by the donut type baffle plates 202. Heretofore, the shell is possibly provided at the center thereof with a tie rod and spacer and the donut type baffle plates 202 support all the reaction tubes 204. By disposing the reaction tubes 204a, illustrated in FIG. 2, in at least one row inside the donut type baffle plates 202, it is possible to increase the number of reaction tubes accommodated in the shell of a fixed diameter, decrease the power energy for the heating medium, and moreover secure the same thermal removal efficiency as before. Though the reason for this achievement is not clear, it is considered that by providing an empty space at the center of the shell and arranging the reaction tubes not supported by the donut type baffle plates 202, pressure drop of the heating medium is decreased, hence it leads to reduce power energy, enhances the linear velocity to improve heat exchange rate, and succeeds in decreasing the hot spot temperature and securing the selectivity in the same way as before.

Properly, the cross sectional area of the empty space is in the range of 0.5–5%, preferably 1–4%, and particularly preferably 1–2%, based on the cross sectional area of the shell. If this cross sectional area is less than 0.5%, the shortage will be at a disadvantage in impairing the flow of the heating medium around the central part, becoming insufficient in the heat removal of the reaction tubes, and failing to decrease the hot spot temperature. Conversely, if this cross sectional area exceeds 5%, the excess will be at a disadvantage in suffering the shell to acquire an unduly large diameter and lowering the heat efficiency on account of a decrease in the linear velocity. In addition to the tie rod in the central part of the shell 201, a plurality of tie rods and spacers may be disposed, when necessary, as through the donut type baffle plates 202 so as to fix the donut type baffle plates 202 and the disc type baffle plates 203.

Commendably, the cross sectional area of the disc type baffle plates 203 is in the range of 50–95%, preferably 60–90%, and particularly preferably 70–85%, based on the cross sectional area of the shell 201. If the cross sectional area is less than 50%, the shortage will bring the disadvantage of impairing the flow of the heating medium near the inner wall of the shell and then degrading the thermal efficiency. If the cross sectional area exceeds 95%, the excess will entail the disadvantage of increasing the power energy, impairing the flow of the heating medium near the disc type baffle plates and lowering the thermal efficiency.

Properly, the cross sectional area of holes in the donut type baffle plates 202 is in the range of 2–25, preferably 4–20%, and particularly preferably 6–18%, based on the cross sectional area of the shell. If this cross sectional area is less than 2%, the shortage will enlarge pressure drop of the heating medium. Conversely, if the cross sectional area exceeds 25%, the excess will render the uniform removal of heat difficult.

Figure 2:
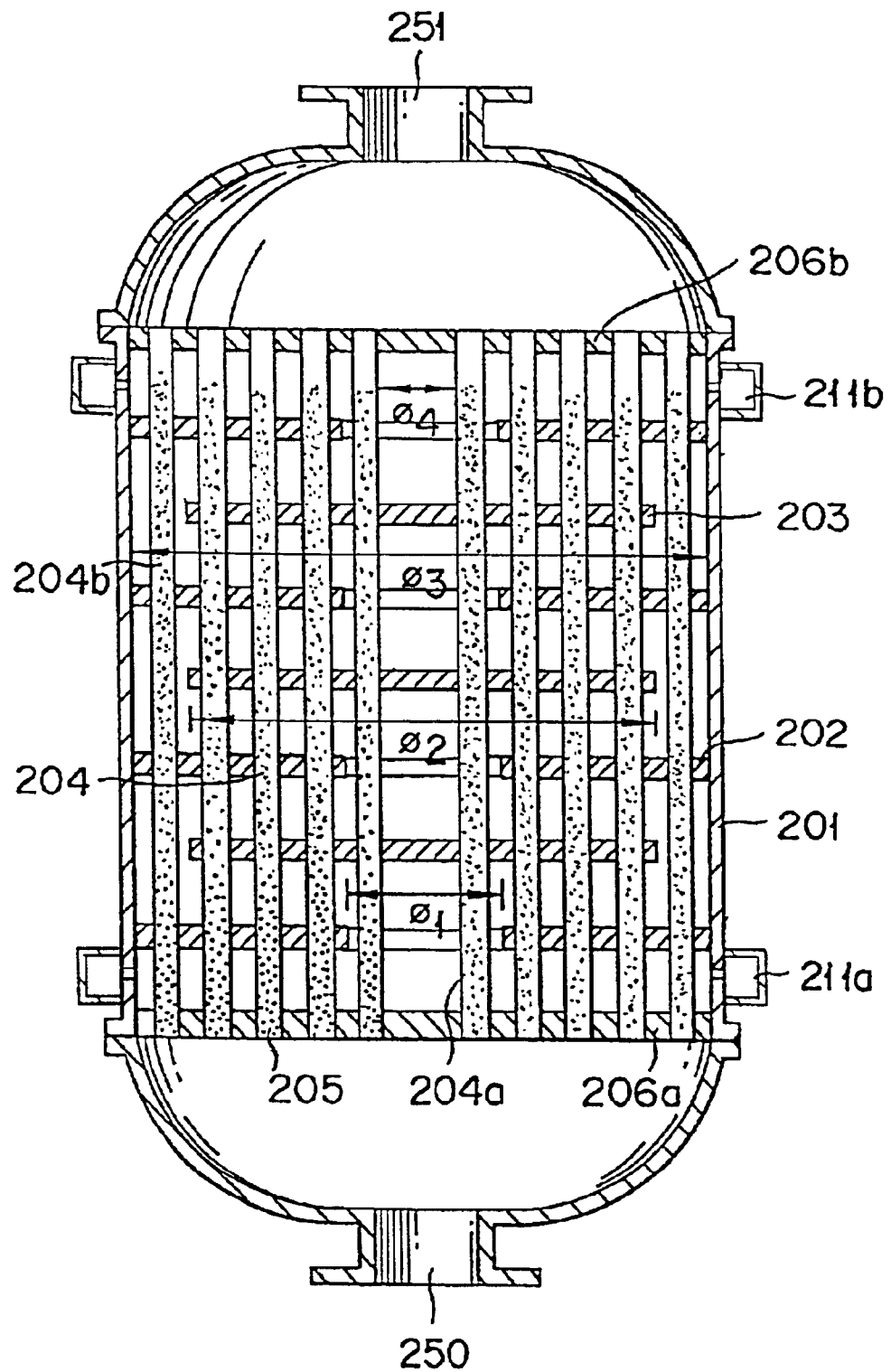
FIG. 2 is a cross sectional diagram illustrating donut type baffle plates, disc type baffle plates, reaction tubes, and an empty space of a reactor of this invention.

This invention embraces such reaction tubes 204a not supported by the donut type baffle plates 202. It may embrace such reaction tubes 204b not supported by the disc type baffle plates as well as illustrated in FIG. 2. If such reaction tubes 204b are arranged, the number of reaction tubes is increased in the shell 201. It is now possible to decrease the hot spot temperature and secure the yield of a desired product as coupled with the choice of the empty space at the center, the area of holes in the donut type baffle plates, and the area of the disc type baffle plates at specific ratios.

Commendably, baffle plates are disposed so as not to overlap the position of hot spot, or rather depart from the position by a distance of not less than 100 mm, preferably not less than 200 mm, from the hot spot. If the hot spot position of reaction tubes overlaps the supporting parts of baffle plates, the efficiency of heat removal by the heating medium will be lowered and the decrease of the hot spot temperature will become difficult. Such hot spot positions can be found by supplying the raw material gas to the reaction tubes packed with a catalyst and measuring the temperatures at various points of the reaction tubes. When the hot spot position is varied in consequence of the advance of reaction, the baffle plates may be properly disposed in consideration of the areas of such variations.

Figure 3:
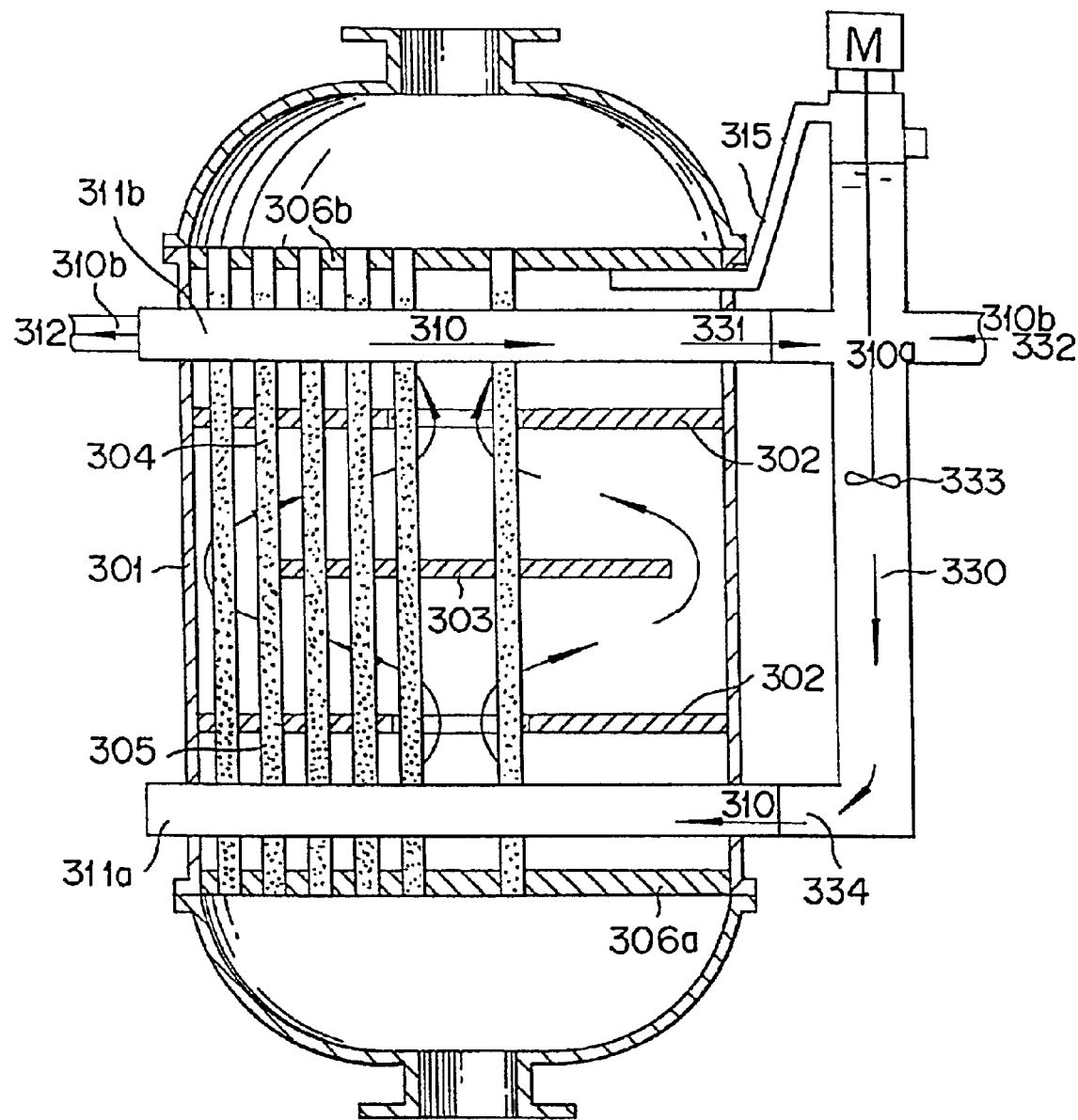
FIG. 3 is a partly sectional diagram illustrating a circulation path for a heating medium in the reactor provided with a circulation device.

In the present reactor, a heating medium 310 is wholly or partly discharged into an annular conduit 311 through a heating medium outlet formed in an annular conduit 311a or 311b and circulated into the shell 301 through the other annular conduit 311b or 311a through a circulation device disposed between the annular conduits 311a and 311b. When the reactor has the circulation device, the heating medium 310 which has the passage thereof secured by the donut type baffle plates 302 and the disc type baffle plates 303 is introduced up-flow from the lower to the upper parts of the reactor. The flow of the heating medium 310 in the reactor will be described below with reference to FIG. 3. In FIG. 3, the reactor is vertically cut but the annular conduits are not cut, in order to show the flow of heating medium.

Of the heating medium 310 introduced through the annular conduit 311a and discharged through the annular conduit 311b, the portion which is not taken out from the shell 301 and a circulation device 330 and is immediately directed toward a heating medium outlet 334 (the portion referred to as a "heating medium 310a") is introduced into the circulation device 330 via a heating medium circulation port 331 formed in the annular conduit 311b, further introduced into the annular conduit 311a through the heating medium outlet 334, and circulated into the shell 301.

Figure 4:
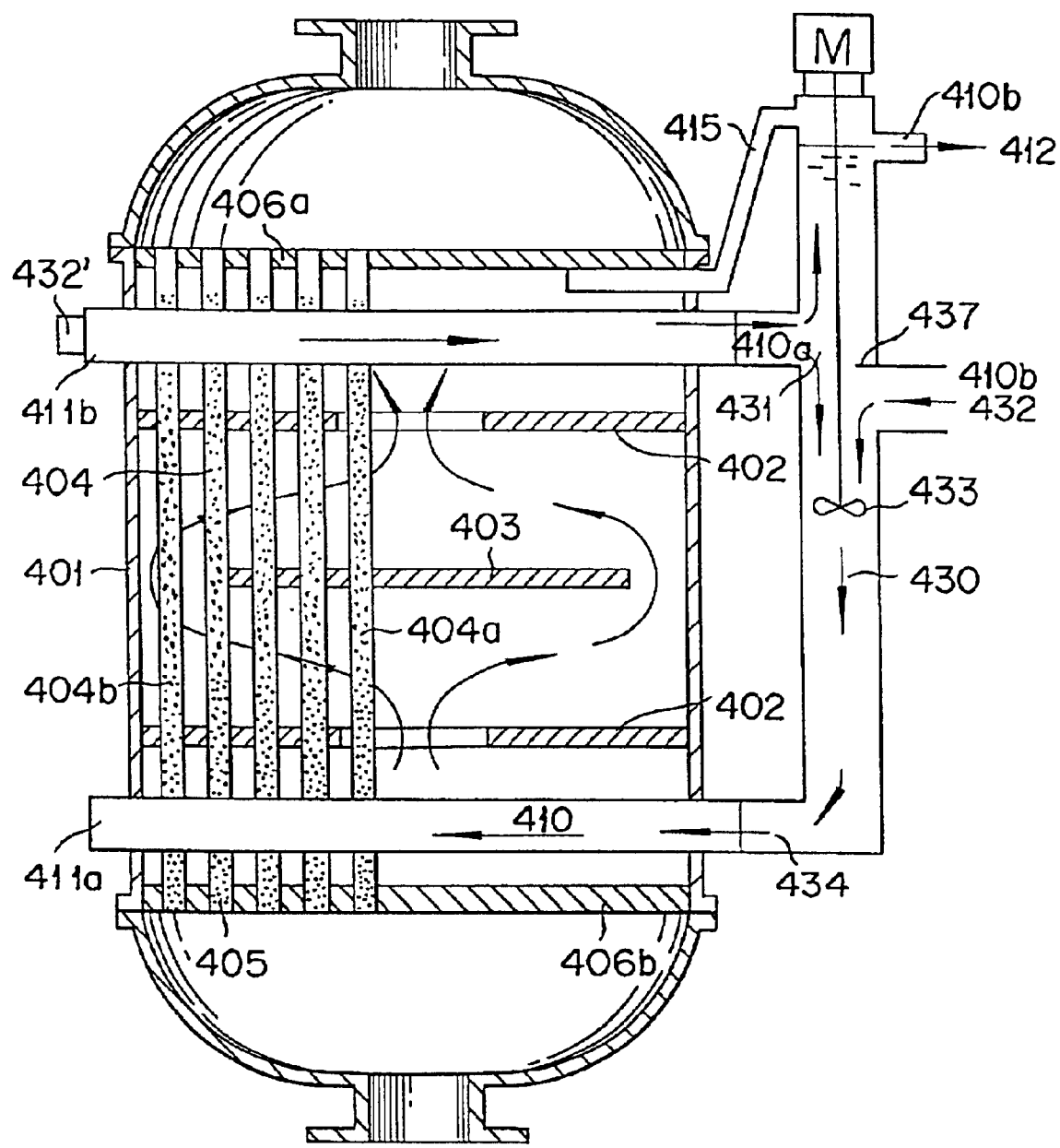
FIG. 4 is a partly sectional schematic diagram of a reactor taken out the heating medium from part of the circulation device and introducing the heating medium in a cooled state to the circulation device.

Meanwhile, part of the heating medium 310 is withdrawn from the shell 301 through a heating medium withdraw port 312 formed to the annular conduit 311b, cooled in a heat exchanger (not shown), and introduced through a heating medium inlet 332 formed opposite the heating medium circulation port 331 of the circulation device 330. The discharge of the heating medium 310 out of the shell is not relied solely on the annular conduit 311b. It may be otherwise accomplished, as illustrated in FIG. 4, for example, by introducing the heating medium into a circulation device 430 from an annular conduit 411b via a heating medium circulation port 412, then withdrawn it from a shell 401 via the heating medium withdraw port 412 formed in the upper part of the circulation device 430, cooling it by a heat exchanger (not shown), and introducing the cooled heating medium via a heating medium introduction port 432 formed in the circulation device 430. In FIG. 4, the reactor is vertically cut but the annular conduits are not cut, in order to show the flow of heating medium. By withdrawing the heating medium from the shell, cooling it, and then circulating the cooled heating medium 410b to the proximity of the annular conduit 411b or a heating medium circulation port 431 of the circulation device 430, the heating medium 410a and the cooled heating medium 410b are mixed readily because those supply parts thereof adjoin. The heating medium withdrawn from the heating medium withdraw port 412, illustrated in FIG. 4, when necessary, may be circulated into the shell via the annular conduit 411b, for example. In this case, they must be given a sufficiently long retention time within the annular conduit 411b to ensure thorough mixing. The annular conduit 411b is preferred to provide, at the position opposite the heating medium circulation port 431, with a heating medium introduction port 432'. The heating medium introduction port 432 where the cooled heating medium 410b is introduced into the annular conduit 411b is depicted as the reference numeral 432' in FIG. 4. In this case, the heating medium introduction port 432 illustrated in FIG. 4 is absent. Thus, the present reactor is preferred to have the heating medium introduction port 432 for introducing the cooled heating medium 410b into the shell 401 or the circulation device 430 in the proximity of the heating medium circulation port 431 of the annular conduit 411b or the circulation device 430. If the cooled heating medium 410b is circulated to the proximity of the heating medium discharge port 434 of the circulation device 430, this circulation brings disadvantages such as preventing the heating medium 410a and the cooled heating medium 410b from being thoroughly mixed, impairing the uniformity of temperature distribution of the heating medium 410 circulated in the shell 401, and tending to generate locally abnormal high temperature in the reaction tube 404. According to this invention, the heating medium 410a and the cooled heating medium 410b are mixed very efficiently by supplying the cooled heating medium (heating medium 410b) to the heating medium circulation port 431 in the circulation device 430 and providing, in part of the annular conduit 411b, with the heating medium introduction port 432. Further, since the amount of the heat removed by the heating medium during the transfer in the circulation device 430 is extremely small, the heating medium is capable of thoroughly removing the reaction heat. Moreover, by using the heating medium 410 of uniform temperature distribution, it is possible to prevent evenly the abnormally high temperature of the hot spot and reduce the amount of the heating medium to be circulated.

When the heating medium introduction port for admitting the cooled heating medium is disposed inside the circulation device, the position opposed to the heating medium circulation port 331 may be cited as shown in FIG. 3. When the heating medium withdraw port 412 is disposed on the upper part of the circulation device 430 as illustrated in FIG. 4, it entails disadvantageous of the thermal efficiency that when the heating medium 410b is introduced through the position opposed to the heating medium circulation port 431, part of the cooled heating medium 410b is withdrawn out of the reactor through the heating medium withdraw port 412. In this case, the position nearest to the heating medium circulation port 431 inside the circulation device 430 and farthest from the heating medium discharge port 434, i.e. the outlet for discharging the heating medium from the circulation device into the reactor may be cited. When the circulation device is provided therein with a plurality of heating medium circulation ports 431, the heating medium 410b may be introduced near any of the ports. Such positions invariably allow the cooled heating medium 410b and the heating medium 410a to be efficiently mixed.

Further, in this invention, the heating medium introduction port 432 may be disposed in part of the annular conduit on the outlet side of the reactor which conduit is connected to the heating medium circulation port of the circulation device. This choice is commendable because the heating medium 410a and the cooled heating medium 410b have been already mixed by the time that they are introduced into the circulation device 430 and the preparation of the heating medium 410 of uniform heat distribution is readily attained in the circulation device 430. In this case, the position of the heating medium introduction port 432 is preferred to oppose to the circulation device 430 so as to allow the mixed heating medium a sufficiently long retention time in the annular conduit.

When the heating medium is circulated up-flow as illustrated in FIG. 4, it may be withdrawn through the heating medium withdraw port 412 disposed in the upper part of the circulation device 430 by the use of a pump 433. In this case, it is commendable to provide a partition plate 437 so as to prevent the heating medium so withdrawn from being mixed with the cooled heating medium 410b introduced through the heating medium introduction port 432 disposed thereunder.

In the present reactor, the circulation device 430 may be provided therein with an agitator instead of the pump 433 for the purpose of efficiently mixing the heating medium 410a and the cooled heating medium 410b. The use of this agitator promises the heating medium of more uniform heat distribution. The heating medium 410 (heating medium 410a+ cooled heating medium 410b) acquired uniformed heat distribution is introduced again from the annular conduit 411a into the shell 401 via the heating medium discharge port 434 of the circulation device 430. The flows of the heating medium 410 (410a+410b), the heating medium 410a, and the cooled heating medium 410b are indicated in the diagram by the relevant reference numerals overlying the arrow marks which show the respective passages.

The heating medium 410b withdrawn from the shell 401 is preferred to undergo gas-liquid separation either before or after the heat exchange in the present invention. The gas-liquid separation is commendable because the use of the heating medium 410b entraining air bubbles tends to produce a pool of gas underneath the upper tube sheet inside the shell and because the uniform mixture of the heating medium 410a and the cooled heating medium 410b can be readily obtained using the deaerated heating medium. The methods available for the gas-liquid separation include a method which prevents the gas from being trapped into the liquid by decreasing the velocity or adjust the height of liquid as well as other methods.

The present reactor is provided with the annular conduits 411a and 411b which have through openings disposed intermittently throughout the entire circumference thereof. The use of these conduits is commendable because the heating medium can be evenly supplied and the hot spot temperature reduced efficiently by supplying and discharging the heating medium evenly in the whole circumferential direction of the reactor through the annular conduits 411a and 411b. In this case, the annular conduits are preferred to provide with a plurality of rows of through openings of the heating medium.

Figure 5:
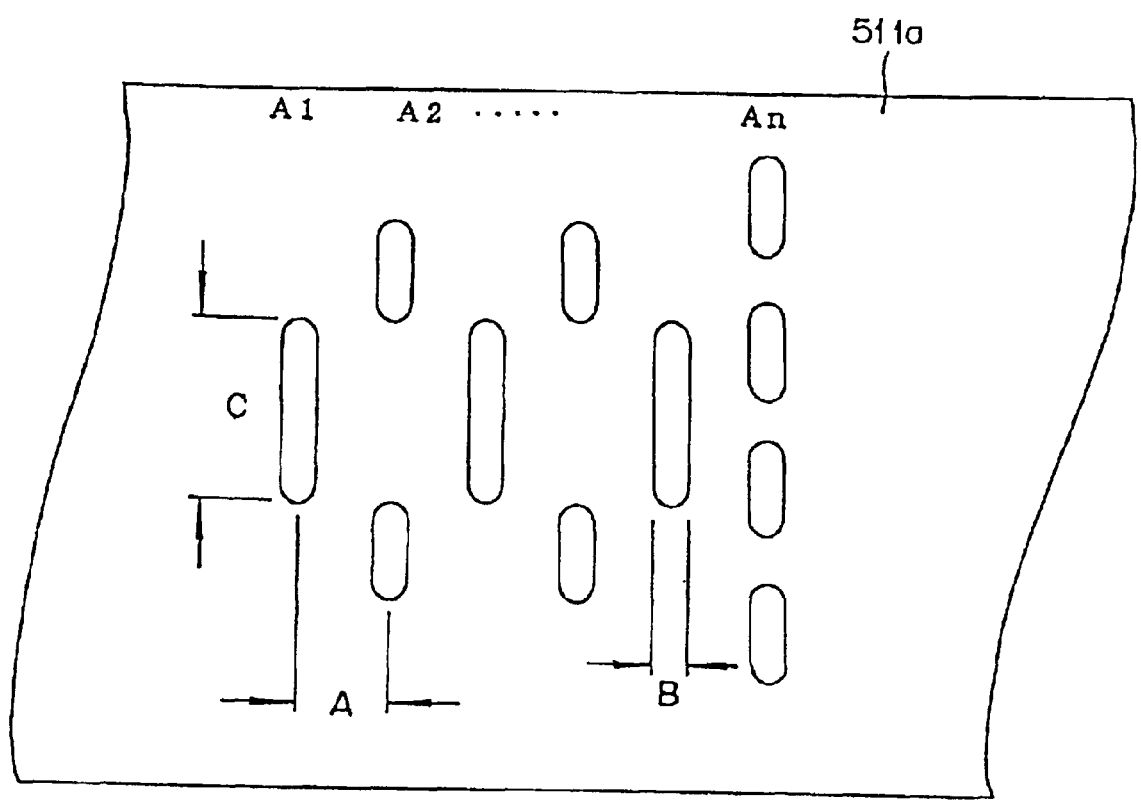
FIG. 5 is a diagram illustrating an opening row in an annular conduit.

With reference to FIG. 5, an annular conduit 511a has a plurality of opening rows A1 and A2. The center distance A in each opening rows may be equal or not equal in a given row. Properly, they are in the range of 50–500 mm, preferably 100–400 mm, and particularly especially 200–300 mm. If it is less than 50 mm, manufacture of the annular conduits will become unduly difficult. If it exceeds 500 mm, the annular conduits will encounter difficulty in forwarding the heating medium uniformly into the shell. The number of openings in each row is at least one. As depicted in FIG. 5, a row A1 has one opening, a row A2 two openings, and a row An four openings. Since the numbers of openings in the individual rows are different, distances between these adjacent openings do not coincide with the center distance A. The width B of an opening is properly in the range of 5–50%, preferably 10–40%, and particularly preferably 20–30%, based on the center distance A. If the opening width is less than 5%, the annular conduit will suffer an undue addition to height. If it exceeds 50%, the openings will have such an unduly low height as to render difficult the introduction of heating medium throughout a wide region of conduit. Further, the ratio of the opening length C/opening width B is preferred to be in the range of 0.2–20. The center distance A does not need to be identical in all the annular conduits. By the same token, the opening width B does not need to be identical in all the annular conduits. By providing the annular conduits each with a plurality of openings, it is possible for the conduits to pass the heating medium evenly in and out. The openings are not particularly restricted, but may include for example circle, oval, ellipsis, and rectangle.

In the modes as depicted in FIGS. 3 and 4, the heating mediums 310 and 410 are moved up-flow, no matter whether the raw material is supplied up-flow or down-flow. When the present reactor performs a catalytic gas phase oxidation, the raw material gas may be introduced up-flow or down-flow into the reaction tubes 304 and 404 without any particular restriction. The heating mediums 310 and 410 may be introduced in co-current or counter flow relative to the supply of the raw material without any particular restriction.

Further, the present reactor prefers a gas discharge pipe for discharging the gas collected in the upper parts of the shells 301 and 401 to be tightly joined with the tube sheet. Generally, when the heating mediums 310 and 410 are introduced into the respective shells 301 and 401, they tend to bring a gas therein and form an empty space devoid of the heating medium in the upper parts of the shells 301 and 401. Since this gas pool is devoid of the heating medium, it locally obstructs the thorough removal of heat and then induces abnormal rise of temperature. By providing the gas discharge port, it is possible to expel the gas that would possibly form the pool, fill the space with the heating medium, prevent the reaction tubes from giving rise to local abnormal rise of temperature, and stabilize the reaction conditions.

Then, the present reactor operated by introducing the heating medium down-flow will be explained below with reference to FIG. 6. A reaction tube 604a not supported by donut type baffle plates 602 is disposed in the central part of a reactor shell. A cooled heating medium 610b is introduced through a heating medium introduction port 632 into a circulation device 630. The heating medium discharged through a heating medium withdraw port 612 formed in an annular conduit 611a is pushed up to a heating medium discharge pot 613 disposed above an upper tube sheet 606b of the shell 601 and then discharged from the system through a nozzle 614. In this case, the same amount of a cold heating medium as the heating medium 610b which has been discharged from the system by the heating medium discharge pot 613 is supplied through the heating medium introduction port 632. As a result, the shell 601 can secure the state of being filled with the heating medium 610. The heating medium 610b which has been withdrawn from the shell, cooled, and then put to circulation for reuse and the heating medium 610a which has been introduced into the circulation device 630 through a heating medium circulation port 631 (the heating medium which is not withdrawn from the shell and which is immediately circularly used) may be mixed and scooped up by a pump 633 such as an axial-flow or volute pump and then introduced from a heating medium discharge port 634 into the shell 601 via the annular conduit 611b. The amount of the heating medium so introduced may be adjusted within the range of amount of the heating medium to be circulated.

The present reactor, in any of the modes conceivable, can supply a heating medium to the shell 601 and discharge it from the shell via the annular conduits 611a and 611b disposed, respectively, in the upper and lower peripheral parts of the reactor. The inflow and outflow of the heating medium 610 may be effected at a plurality of points in the annular conduits 611a and 611b. For this purpose, two or more circulation devices may be installed. The heating medium of a uniform temperature distribution is not easily adjusted by simply increasing the number of pumps. According to this invention, since the heating medium having uniform temperature distribution is supplied within the circulation device, the installation of a plurality of circulation devices results in more efficient removal of heat.

Further, the present reactor is enabled to secure the state of being filled with the heating medium by having back-pressure imparting devices disposed before and after the withdraw port for the heating medium and imparting satisfactory back-pressure to the heating medium flowing down the shell. While the heating medium 610b is withdrawn from the shell 601, the interior of the shell 601 is preferred to retain the state of being filled with the heating medium 610. By disposing the back-pressure imparting devices and imparting satisfactory back pressure to the heating medium flowing down in the shell, the shell can be fully filled with the heating medium. Suitable examples of the back-pressure imparting device may include a resistant orifice, valve, and heat exchanger. The present reactor can be further provided with such a back-pressure imparting device.

Figure 6:
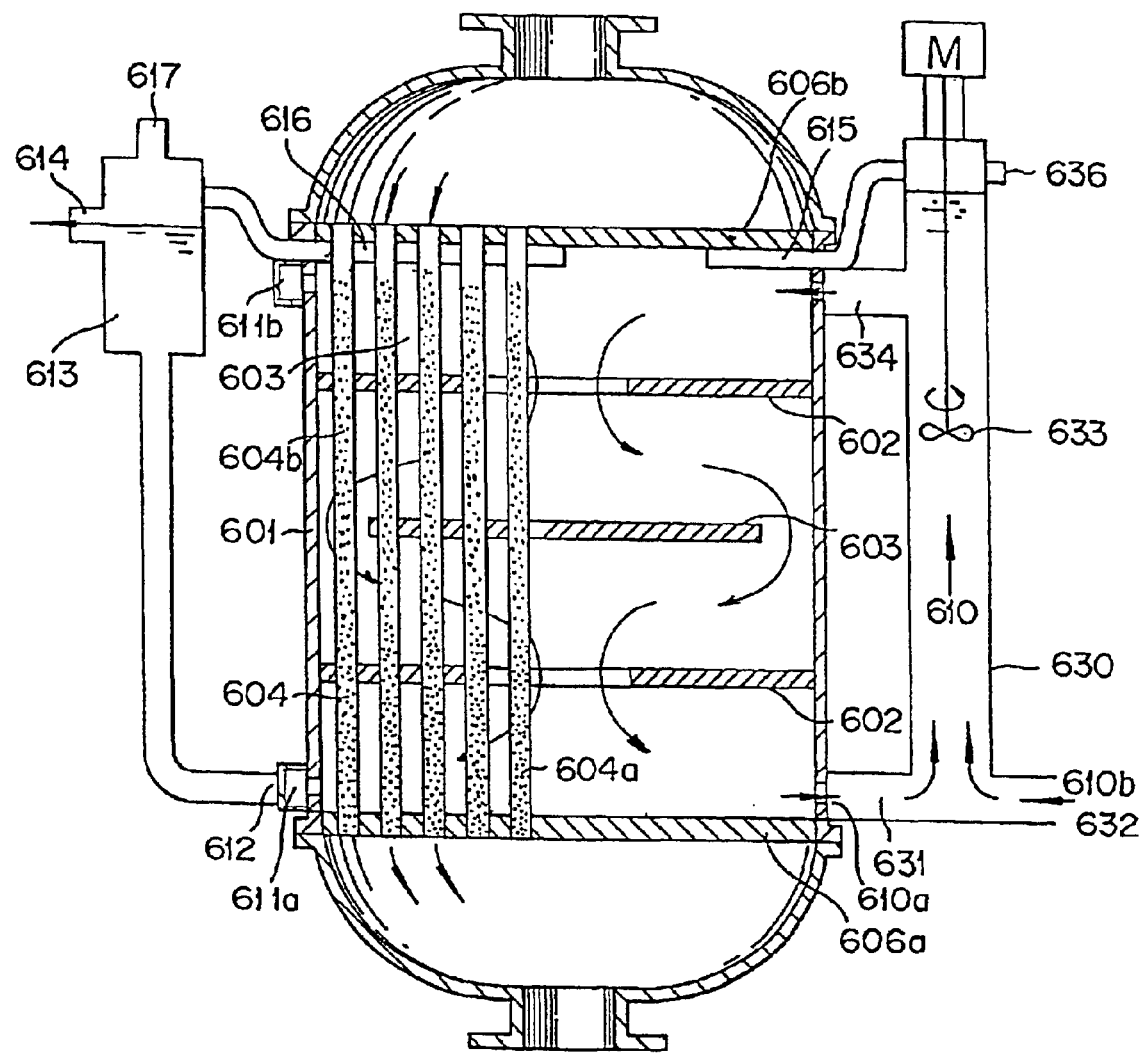
FIG. 6 is a sectional diagram illustrating the flow of a heating medium in the reactor adapted to pass the heating medium in a down-flow pattern.

In FIG. 6, when the gas entrained by the heating medium during the supply of heating medium to the upper part of the shell 601 is collected and forms a pool in the interior of the shell, the gas in the pool may be extracted through a pipe 616 inserted to the central part of upper part of the shell 601 into the heating medium discharge pot 613 or through a pipe 615 laid at the periphery of the reactor into an upper empty space of the heating medium circulation device 630. The formation of the gas pool within the shell 601 which gas pool constitutes itself the factors for impairing the uniformity of the heat removal from the reactor and inducing an abnormal reaction can be then prevented. The gas may be discharged through a gas discharge port 617 by allowing the gas discharge conduit 616 disposed on the upper part of the shell 601 to communicate with the gas phase part of the heating medium discharge pot 613 situated above the upper tube sheet or the gas may be discharged into the upper empty space of the circulation device 630 having a gas discharge conduit 636.

Figure 7:
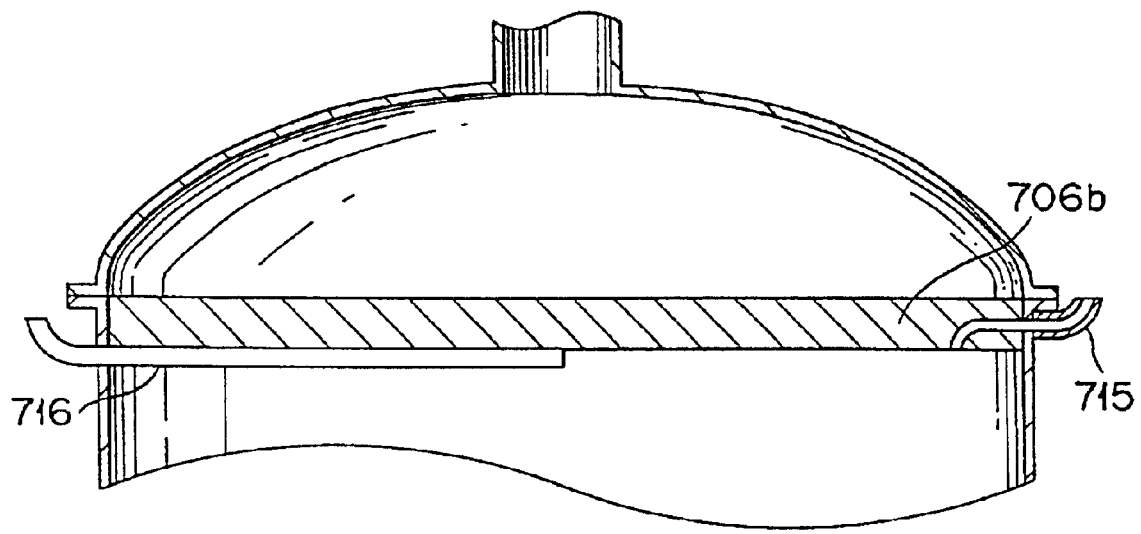
FIG. 7 is a sectional diagram illustrating the configuration of gas outlet in an upper tube sheet.

FIG. 7 illustrates examples of the arrangement of gas discharge conduits. The gas collected on the upper periphery of the reactor may be discharged by forming a passage 715 in an upper tube sheet 706b to establish continuity between the interior and exterior of the shell. The gas collected in the central part of the reactor may be discharged by means of a gas discharge conduit 716 disposed directly below the upper tube sheet 706b.

Now, the method for forming (meth)acrylic acid or (meth) acrolein by the reaction of catalytic gas phase oxidation of a gas containing propylene or isobutylene by the use of the present reactor will be described below with reference to FIG. 2.

The reaction of catalytic gas phase oxidation contemplated by this invention is effected by supplying a raw material gas to the reaction tubes 204 filled with the catalyst 205. The raw material gas of admixture of the reactants with air etc. is introduced from a raw material gas supply port 250 into the reaction tubes 204 packed with the catalyst 205 in the shell 201, oxidized in the reaction tubes into the reaction product, and discharged through a formed gas (product) discharge port 251.

This invention can be applied to a reactor in which upper and lower chambers are formed by an intermediate tube sheet.

Suitable heating mediums to be circulated in the shell may be any of the known heating mediums, but may include, for example, a molten salt, niter, and phenyl ether type heating medium, which is the Dowtherm type organic heating medium.

According to this invention, by disposing such reaction tubes as are not supported by the areas of donut type baffle plates, it is possible to decrease the electric power of an axial-flow pump to, for example, 1/5.4.

According to this invention, the power energy can be reduced and the selectivity and yield of the desired product can be maintained constant by forming an empty space in the central part of shell and disposing reaction tubes not supported by donut type baffle plates. Further, since the hot spots of reaction tubes can be uniformly reduced, it is possible to prevent the deterioration of catalyst efficiently and elongate the service life of catalyst.

(II) Means for Providing Circulation Passage for Heating Medium

The construction of (I) mentioned above is preferred to be additionally provide a circulation passage for heating mediums.

The term "circulation passage" as used herein refers to the part having no reaction tubes in the shell between the upper and lower tube sheets and between the peripheral and central parts of the shell in the cross section thereof. The reactor is provided with at least one circulation passage, though it is preferred to provide at least two passages. The term "peripheral part" as used herein refers to the empty space between the inner wall of the shell and the reaction tubes (group). The heating medium can advance this circulation passage substantially and horizontally because of the presence of baffle plates in the reactor preferentially from the peripheral part to the central part of the reactor or from the central part to the peripheral part of the reactor, as compared with the region in which the reaction tubes are present. Where a plurality of circulation passages are present, the widths of individual circulation passages may be identical or not. Those widths are preferred to be substantially identical from the viewpoint of facilitating the control of flow rate of the heating medium.

The reaction tubes are preferred to be so configured that the difference in the number of reaction tubes among the individual regions divided by at least two circulation passages falls within 3%. If this difference exceeds 3%, the excess will be at a disadvantage in generating distribution of the flow rates of heating medium among the regions of reaction tubes, inducing differences in temperature distributions, and rendering the control of reaction difficult. A method for configuring the reaction tubes in the reaction tube regions is not particularly restricted so long as it gives rise to no circulation passage, but the reaction tubes may be configured regularly or irregularly. The expression "difference in the number of reaction tubes in the individual regions of reaction tubes" as used herein refers to the absolute value given by the formula:

{(Number of reaction tubes in the individual regions)/(average number of reaction tubes in the regions)−1}×100.

The cross-sectional area of circulation passages is preferred to be in the range of 0.5–5%, of the total cross-sectional area of the reactor. The term "cross-sectional area of the circulation passage" as used herein is expressed as $\{(D-d)/2\} \times B \times N$, provided the passage is a linear strip of a same width, wherein D denotes the diameter (inside diameter) of shell of the reactor, d the center diameter (diameter of the central empty space), N the number of circulation passages, and B the width of the circulation passage (provided the relation of B>((pitch of reaction tubes)−(outside diameter of reaction tubes)) is satisfied). The cross-sectional area of the reactor refers to the whole cross-sectional area of the reactor $\{(\pi/4)D^2\}$, i.e. the total of the central part, the peripheral part, the circulation passages and all the regions seating the reaction tubes. If the cross-sectional area is less than 0.5%, the amount of the heating medium to be circulated through the circulation passages will be unduly small and the temperature distribution of the heating medium within the reactor will not be satisfactorily eliminated. Conversely, if it exceeds 5%, the excess will be at a disadvantage in unduly increasing the amount of the heating medium to be passed through the circulation passage and then giving rise to uneven temperature distribution such that the temperature is low near the circulation passages and high in the other part.

The number of circulation passages is properly at least one, preferably not less than two, and more preferably three to six, per reactor. If the number of circulation passages is unduly small, the effect of enabling the heating medium to pass through the circulation passages throughout the entire reactor will not be always obtained fully satisfactorily. Conversely, if the number is unduly large, since the ordinary pitches of reaction tubes (distance between the adjacent reaction tubes) approach, the excess will be at a disadvantage in reducing the amount of the heating medium passed through the circulation passages and then increasing the heat influence from the reaction tubes.

Heretofore, it has been considered that the heating medium, in the absence of circulation passages, flows while contacting the individual reaction tubes, removes the reaction heat efficiently, and makes the temperature distribution within the reactor uniform. Unexpectedly the provision of circulation passages brings advantages such as enabling the heating medium to pass quickly through the circulation passages, efficiently lowering the temperature of the heating medium (or elevating the temperature when the temperature in the reaction tubes is low) near the central part or the peripheral part of the reactor, then reducing more the temperature distribution of the whole reactor, and succeeding in enhancing the yield of the desired product.

Now, the present invention will be specifically described below as divided into cases of the flow of heating mediums of (1) up-flow and (2) down-flow, using a reactor of a single chamber and operated by feeding the raw material gas down-flow and (3) using a reactor partitioned into two chambers.

(1) Up-flow

When the reaction of catalytic gas phase oxidation is performed by the use of a shell-and-tube type fixed-bed reactor in the present invention, the raw material gas for the reaction and the heating medium are passed in counter flow by allowing the raw material gas supplied from the upper part of the reactor to flow down the interior of reaction tubes and meanwhile supplying a heat exchange medium (heating medium) from the lower part of the shell.

Figure 8:
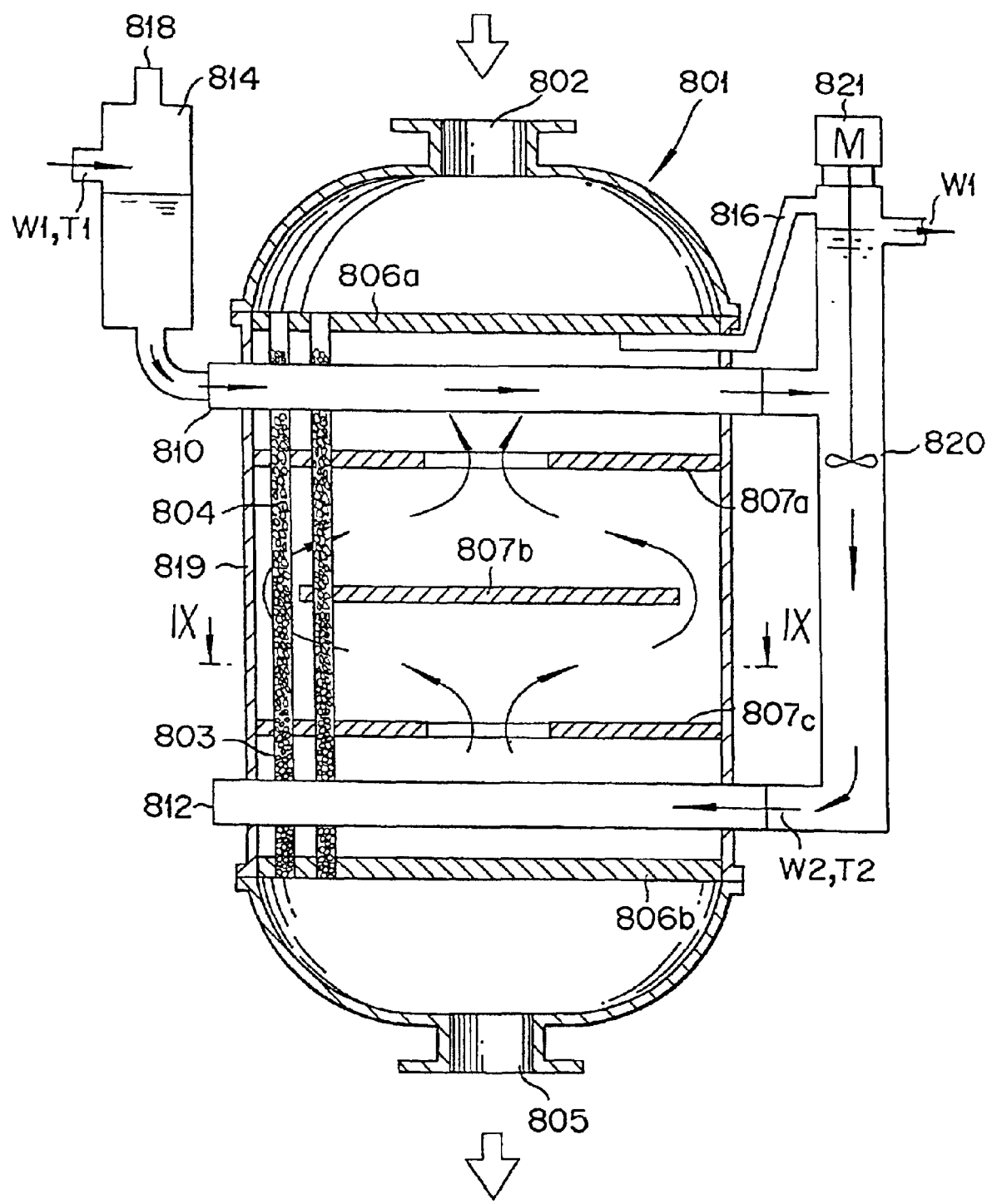
FIG. 8 is a partly sectional schematic explanatory diagram for explaining one example of the reactor of this invention.

FIG. 8 is a schematic explanatory diagram illustrating a typical example of the shell-and-tube type reactor according to this invention. In FIG. 8, the reactor is vertically cut but the annular conduits are not cut, in order to show the flow of heating medium. As illustrated in FIG. 8, the raw material gas mixed from the raw material for the reaction with an oxygen-containing gas is supplied through a raw material gas introduction port 802 to a reactor shell 819, allowed to fall down the interiors of reaction tubes 804 packed with a catalyst 803, partially oxidized into a reaction product in the reaction tubes, and then discharged through a formed gas discharge port 805.

The heating medium is supplied into a reactor 801 in counter flow to the raw material gas via a lower annular conduit 812, used for recovering the reaction heat, and then discharged through an upper annular conduit 810. The annular conduits 812 and 810 are those laid annularly outside the reactor. The heating medium is preferred to pass in and out uniformly in the whole circumferential directions of the reactor through holes (not shown) formed intermittently throughout the entire circumference of annular conduits.

The annular conduits involved herein are preferred to have a plurality of rows of openings capable of passing the heating medium. For further information on the rows, refer to the explanation in FIG. 5.

In the upper annular conduit 810, the heating medium after the recovery of reaction heat and the newly cooled heating medium are mixed to introduce into a circulation device 820. The cooled heating medium (the amount of supply thereof at T1° C. denoted by W1) is preferred to supply to the upper annular conduit 810 after the gas entrained by the heating medium during the supply has been removed in a gas-liquid separator 814 to discharge through a nozzle 818.

Part of the heating medium which has entered the circulation device 820 (the amount of discharge: W1) is forwarded via the upper part thereof to a heating medium vessel (not shown) located outside the reactor, and the other heating medium is supplied from the lower annular conduit 812 to the reactor 801 through a pump 821 such as an axial-flow or volute pump and/or an agitator (the amount of circulation at T2° C. denoted by W2). The heating medium forwarded to the heating medium vessel, when necessary, is advanced to a heat exchanger (not shown) through a pump to remove the heat, and then reclaimed as the cooled heating medium. The heating medium forwarded to the lower annular conduit 812 is capable of recovering the reaction heat from the reaction tubes 804 because the heating medium of relatively high temperature resulting from recovering the reaction heat has been mixed with the cooled heating medium to reduce the temperature thereof. The heating medium is preferred to pass in and out evenly in the whole circumferential direction of the reactor 801 via the through openings disposed intermittently throughout the entire circumferences of the annular conduits 810 and 812. The provision of the annular conduits 810 and 812 brings advantages of enabling the heating medium to be passed in and out through the entire circumference of the reactor 801 and then reducing the temperature deviation of the heating medium inside the reactor 801. More annular conduits may be used in addition to just one set of upper and lower annular conduits.

In the reactor 801, the heating medium advances along baffle plates 807c, 807b, and 807a such as donut type and disc type baffle plates alternately disposed. The heating medium, for example, advances horizontally from the entire peripheral part of the reactor 801 to the central part, rises past the central part where the donut baffle plate 807c is disposed, then advances in a substantially horizontal state from the central part to the whole peripheral part, further rises past the peripheral part where the disc baffle plate 807b is disposed, and thereafter advances substantially horizontally from the whole peripheral part to the central part. This process is repeated. Though gaps may lie between the donut baffle plate and the wall of reactor, they are preferably eliminated for the purpose of reducing the temperature distribution in the reactor.

When the gas accumulates in the upper part in the shell, the presence of this gas results in obstructing thorough removal of the heat and giving birth to deviation of the temperature of the heating medium. The gas so accumulating is preferred to expel through a nozzle (not shown) using a gas discharge conduit 816.

The discharge of the heating medium which has recovered the reaction heat enables the shell to be filled with the heating medium by forcing the heating medium to above the upper tube sheet of reactor and then withdrawing it from the reactor, for example, through the upper part of the circulation device 820.

Figure 9:
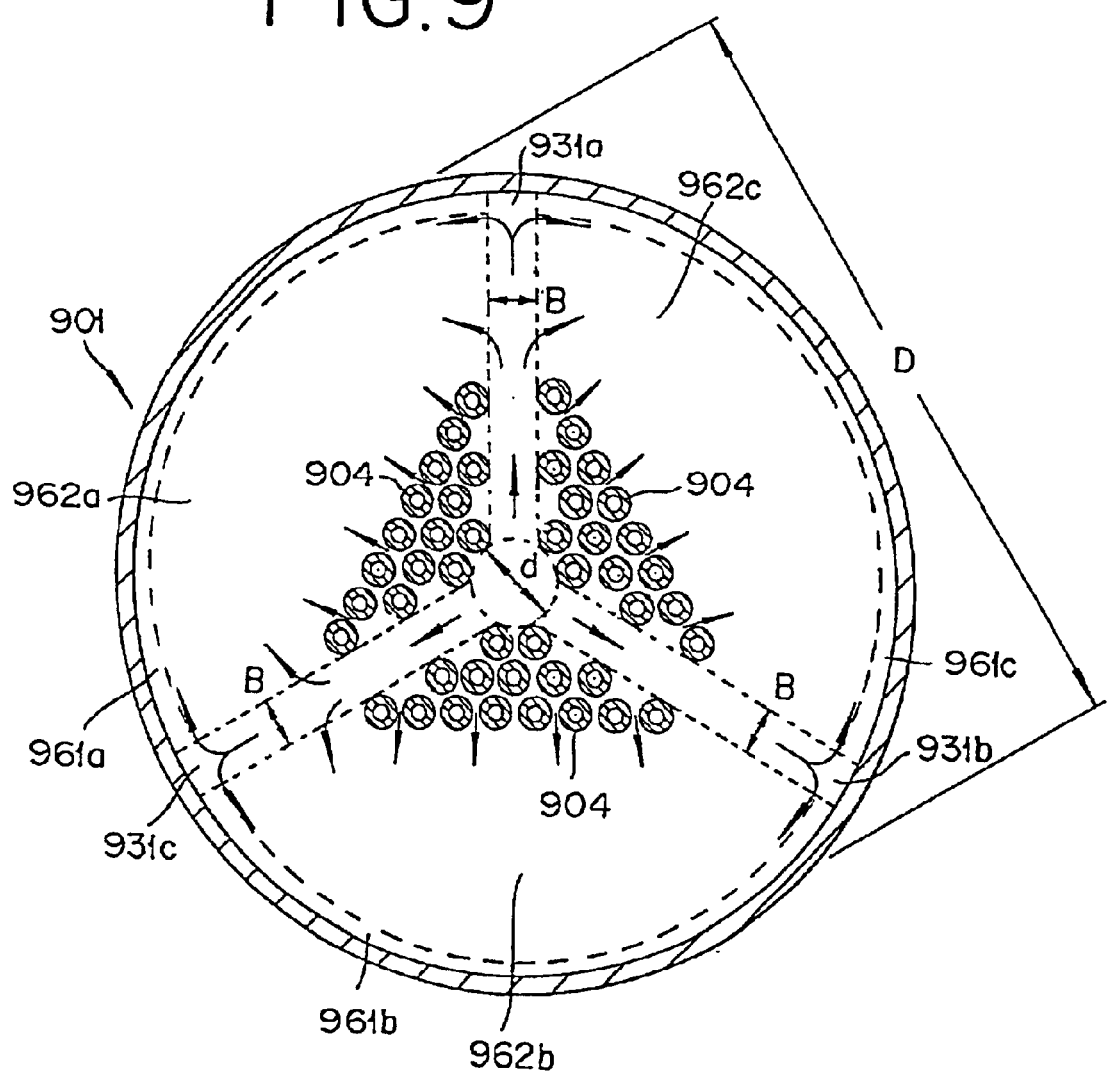
FIG. 9 is a sectional schematic explanatory diagram of a circulation passage in the reactor as taken through FIG. 8 along the line IX—IX.

In accordance with the circulation passages, as illustrated in FIG. 9 (depicting a cross section taken along the line IX—IX of FIG. 8), the heating medium transfers to the peripheral part 961 in a shorter time when it flows through the circulation passages 931a, 931b, and 931c than when it flows through the regions 962 of reaction tubes, though it flows substantially horizontally from the central part to the peripheral part 961 of the reactor 901. The heating medium flowing along the regions 962 of reaction tubes contacts individual reaction tubes 904 and meanwhile recovers the reaction heat and gradually gains in temperature and eventually reaches the peripheral part 961. In contrast, the heating medium passing through the circulation passages 931a, 931b, and 931c can reach the peripheral part 961 in a relatively short time at a relatively low temperature because it does not appreciably contact the reaction tubes 904 and recovers the reaction heat only in a small amount. In the peripheral part 961, the heating medium of relatively low temperature which has advanced through the circulation passages 931a, 931b, and 931c moves in the circumferential direction and mixes with the heating medium of relatively high temperature which has arrived after repeating contact with the reaction tubes, to uniform the temperature on the same cross section.

The above example pertains to the case in which the heating medium flows from the center to the peripheral part of the reactor 901. Now, the case in which the heating medium flows conversely from the whole peripheral part to the central part will be described. The heating medium which passes through the circulation passages has a short time in reaching the central part as compared with the heating medium which advances through the regions of reaction tubes. Specifically, the heating medium which advances through the regions of reaction tubes contacts the individual reaction tubes and meanwhile recovers the reaction heat and gradually gains in temperature and eventually reaches the central part. The heating medium which advances through the circulation passages reaches the central part in a relatively short time at relatively low temperature because it does not appreciably contact the reaction tubes 904. In the central part, the heating medium of relatively low temperature which has advanced through the circulation passages mixes with the heating medium of relatively high temperature which has advanced through the regions of reaction tubes, with the result that the temperature of the heating medium in the direction of flow will be uniformized. The mixture then contributes to the abatement of hot spots.

Though the flow rate of the heating medium which advances through the circulation passages is not particularly restricted, it is commendable to decide the cross-sectional area of the circulation passages so that the flow rate may fall in the range of 2–30%, preferably 5–20%, based on the total flow rate of the heating medium which advances within the shell.

If the temperature of raw material gases is lower than that of heating medium in the inlet part of the reactor, the temperature of the heating medium is lowered till the start of reaction because the heat of the heating medium is spent in elevating the temperature of the gas. The heating medium which advances through the circulation passages reaches the central part at relatively high temperature, whereas the heating medium which advances through the regions of reaction tubes contacts the individual reaction tubes and then undergoes deprivation of the heat required for elevating the temperature of the gas and gradually loses in temperature and eventually reaches the central part. Since these heating mediums are mixed in the central part, the temperature of the heating medium is uniformized in the flow direction in the same manner as described above.

The condition, T2 (inlet temperature of reactor)−T1 (temperature of cooled heating medium)=15–150° C., and the condition, W1/W2=2–40%, prove more favorable because they reduce the deviation of temperature of the heating medium in the peripheral part of inlet of the reactor (lower annular conduit) and permit supply of the heating medium at a uniform temperature to the shell.

(2) Down-flow

When the raw material gas for the reaction is supplied, similarly in (1), from the upper part of the reactor and subjected to a reaction of catalytic gas phase oxidation, the heating medium is likewise supplied from the upper part of shell to effect co-current flow of the raw material gas and the heating medium.

Figure 10:
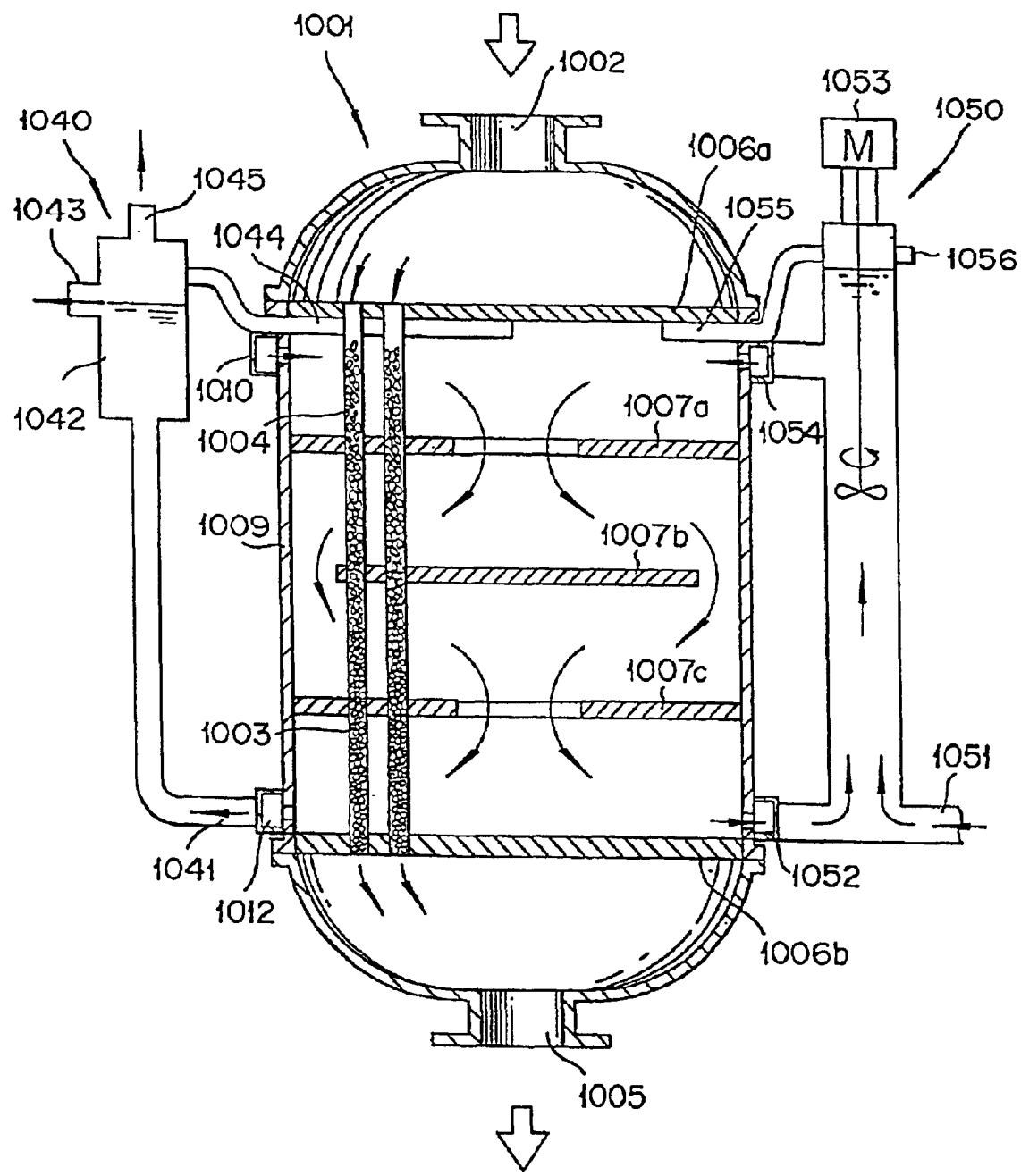
FIG. 10 is a sectional schematic explanatory diagram for explaining one example of the other reactor of this invention.

FIG. 10 is a schematic explanatory diagram illustrating a typical example of the shell-and-tube type reactor according to this invention, wherein 1002 denotes a raw material gas introduction port, 1003 a catalyst, 1004 a reaction tube, 1005 a formed gas discharge port, 1006a an upper tube sheet, 1006b a lower tube sheet, 1007a, 1007b, and 1007c each a baffle plate, 1009 a shell, 1040 a heating medium discharge device, 1041 a heating medium discharge port, 1042 a heating medium discharge pot, 1043 a nozzle, 1051 a cooled heating medium introduction port, 1052 a heating medium discharge port, 1053 a pump, and 1054 a heating medium introduction port.

The raw material gas formed by mixing the raw material for the reaction with air etc. is supplied through the raw material gas introduction port 1002 to a reactor 1001, allowed to flow down into the reaction tubes 1004 packed with the catalyst 1003, to oxidize into the desired product, and then discharged through the formed gas discharge port 1005.

A certain amount of the heating medium which has recovered the reaction heat is withdrawn through the heating medium discharge port 1041 located lower part of the reactor. The withdrawn heating medium is discharged out of the system through the nozzle 1043 via the heating medium discharge pot 1042 disposed above the upper tube sheet 1006a.

The cooled heating medium in the same amount as the heating medium discharged out of the system via the heating medium discharge pot is supplied through the cooled heating medium introduction port 1051. The cooled heating medium and the heating medium recovered through the heating medium discharge port 1052 are mixed by the pump 1053 such as an axial-flow or volute pump and/or an agitator and meanwhile scooped up and supplied into the reactor through the heating medium introduction port 1054. As a result, the shell is fully filled with the heating medium. The supply amount W1 and supply temperature T1 of the cooled heating medium are corrected to fall in the same ranges as in (1) above and are suitably adjusted with the rise of reaction temperature based on the deterioration of catalyst with aging.

The supply of the heating medium toward the shell and the discharge thereof from the shell are preferred to effect uniformly from the whole circumferential direction of the reactor via the through openings disposed intermittently throughout the entire circumferences of the annular conduits 1010 and 1012, respectively, on the upper and lower outer peripheral parts of the reactor.

The reaction tubes are configured substantially in the same manner as illustrated in FIG. 9 and are enabled to prevent deviation of the temperature of the heating medium in the reactor and repress the generation of hot spot temperature.

The method for withdrawing the heating medium out of the reactor is only required to ensure that the shell is fully filled with the heating medium. It is not always required to push the heating medium up onto the upper tube sheet of the reactor and withdraw the heating medium. The state that the reactor is filled with the heating medium may be secured by disposing a back pressure imparting device in or before or after the heating medium discharge port 1041 in the lower part on the shell and imparting thorough back pressure to the heating medium flowing down the reactor. Suitable examples of the back pressure imparting device may include a resistant orifice, valve, and heat exchanger.

Further, when the heating medium advances from the upper part to the lower part of the reactor, the gas introduced as entrained by the heating medium during the supply of heating medium tends to collect in the shell. The gas thus collected in the shell is preferably withdrawn through a pipe disposed between the central part underneath the inner face of the upper tube sheet and the heating medium discharge pot or through a pipe disposed between the periphery of inner face of the upper tube sheet and the upper empty space of the heating medium circulation device. Owing to use of these pipes for withdrawing the gas, the formation of a gas pool in the shell which pool forms the cause for obstructing uniform removal of the reaction heat in the reactor and inducing an abnormal reaction can be prevented.

The withdrawn of the gas, as illustrated in FIG. 10, may be implemented, for example, through a gas discharge port 1045 by establishing communication between the gas discharge conduit 1044 disposed on the upper part of the shell and the heating medium discharge pot 1042 positioned on the upper tube sheet of the reactor or through a nozzle 1056 by allowing a gas discharge conduit 1055 to communicate with the upper empty space of the heating medium circulation device 1050.

Figure 11A:
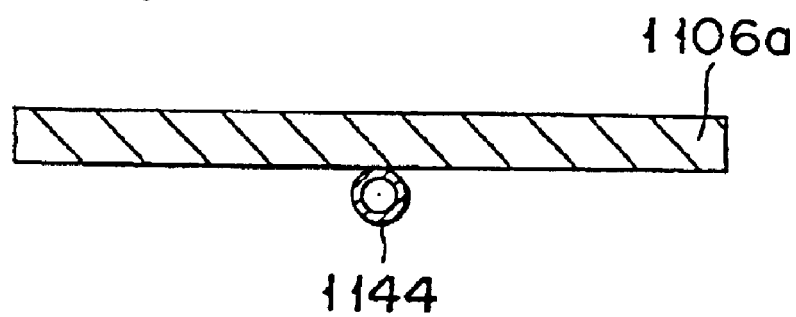
FIGS. 11A and B are sectional explanatory diagrams illustrating examples of the shape of gas outlet conduits.
Figure 11B:
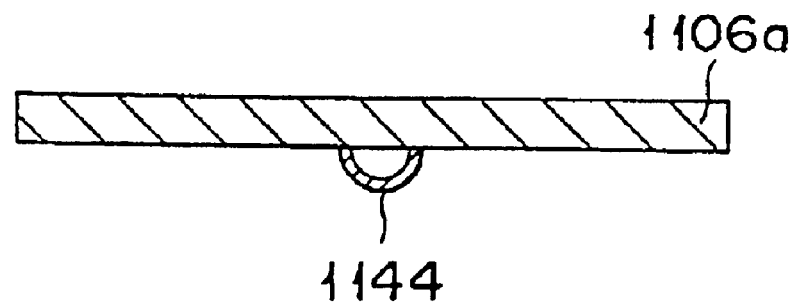

FIG. 7 illustrates examples of the disposition of the gas discharge conduits. As respects the gas collected on the periphery of the reactor, for example, the withdrawal may be effected by forming a passage 715 in the upper tube sheet 706b and completing the continuity of the passage. As concerns the gas collected in the central part of the reactor, the withdrawal may be attained by disposing the gas discharge conduit 716 directly below the upper tube sheet 706b. A gas discharge conduit 1144 for releasing the gas from the central part may be a cylindrical pipe having such a cross section as illustrated in FIG. 11A or a halved pipe as illustrated in FIG. 11B. The halved pipe is commendable because of readily welded to an upper tube sheet 1106a and of readily withdrawal of the gas.

The introduction of raw material gas in down-flow has been described. This invention can be applied similarly to the introduction in up-flow. So long as the temperature of heating medium can be uniformized in the flow direction, the repression of the generation of the hot spot temperature, the improvement of the yield of the desired product, and the elongation of the service life of catalysts can be attained without particularly restricting between the up-flow and the down-flow supply of the raw material gas or the heating medium.

Suitable examples of the heating medium which can be used in this invention include the fused salt which is a popular heating medium and phenyl ether type heating mediums such as Dowtherm.

(3) Reactor Partitioned into Two Chambers

Figure 12:
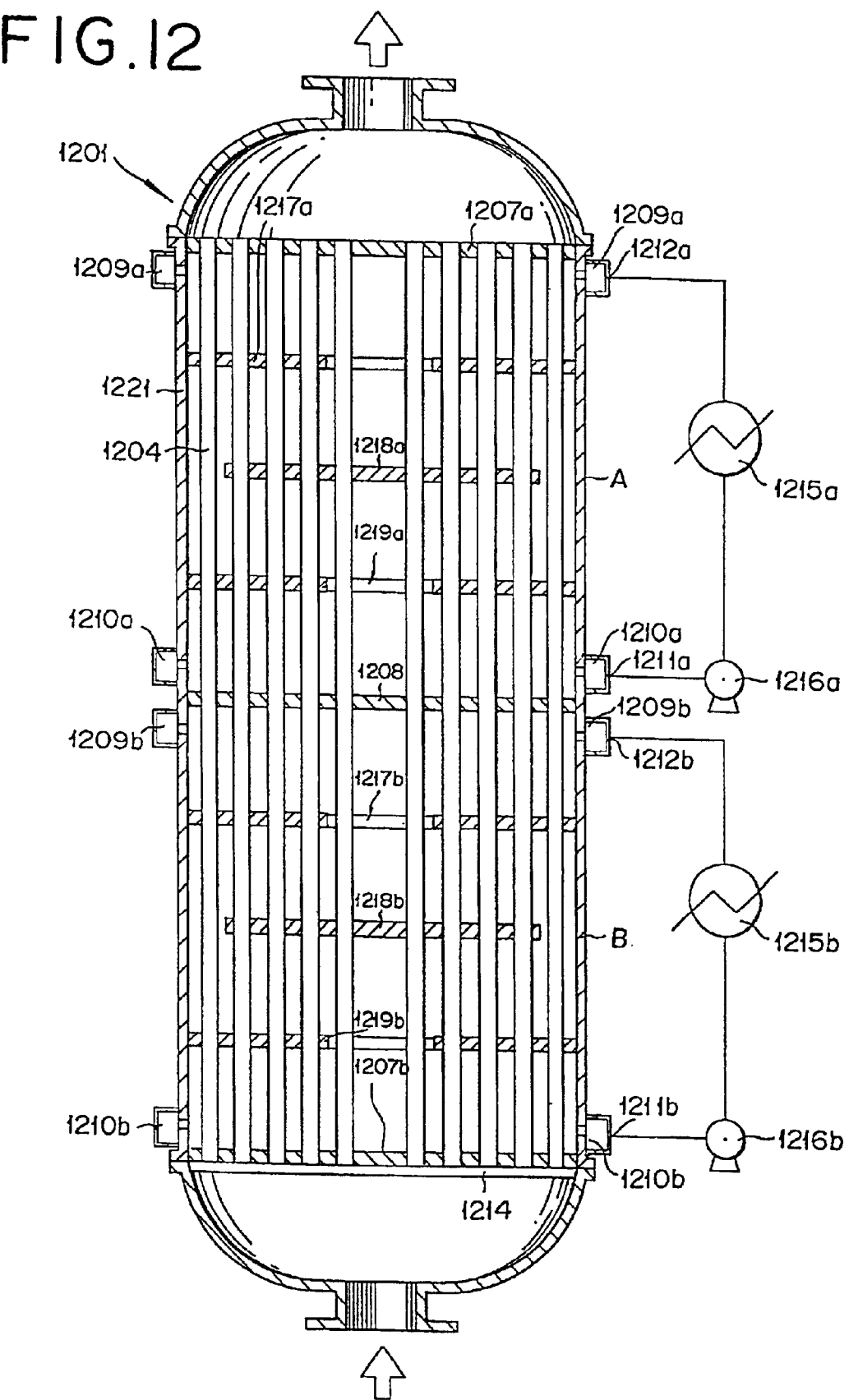
FIG. 12 is an explanatory diagram of one example of the longitudinal section of a two-chamber type reactor for catalytic gas phase oxidation according to this invention.

FIG. 12 is an explanatory diagram illustrating one example of the longitudinal cross section of the reactor according to this invention. The reactor has two chambers A and B. A number of reaction tubes 1204 fill the interior of a reaction chamber 1201 which has a circular cross section in horizontal. These reaction tubes are fastened at their upper ends to an upper tube sheet 1207a and at their lower ends to a lower tube sheet 1207b by a known method such as pipe expansion or welding technique. Further, the reactor 1201 is preferably provided in the central part thereof with a pathway for advancing the heating medium upward from below without installation of the reaction tubes 1204 with a view to ensuring efficient transfer of the heating medium even in the central part. The shell of the reactor 1201 is horizontally partitioned with an intermediate tube sheet 1208 positioned substantially in the middle between the upper tube sheet 1207a and the lower tube sheet 1207b to form two chambers A and B.

Figure 13:
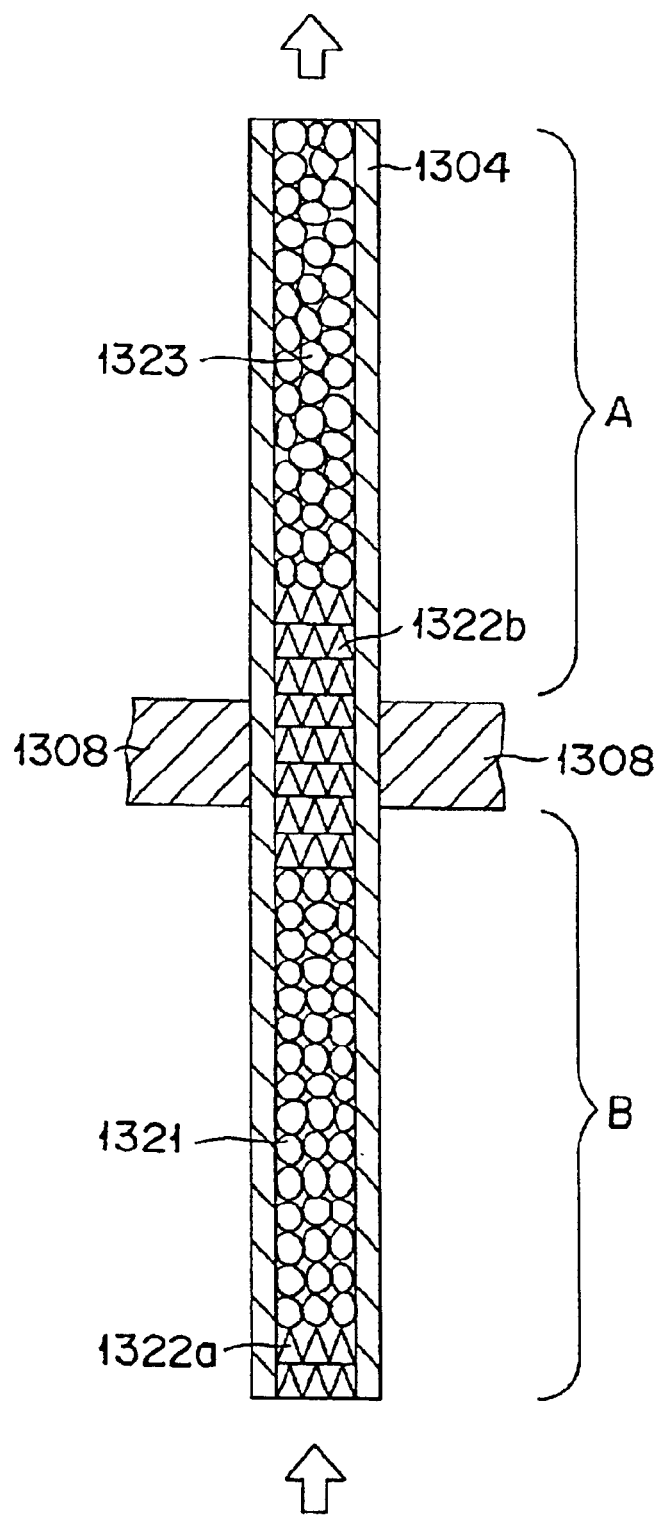
FIG. 13 is a magnified explanatory diagram of the cross section of a catalyst layer in the reaction tube and an intermediate tube sheet shown in FIG. 12.

FIG. 13 is a magnified explanatory diagram of the longitudinal cross section of the catalyst layer and intermediate tube sheet of the reaction tube. The reaction tubes 1304 and the intermediate tube sheet 1308 are preferably made of the same material such as steel or iron in consideration of the possible expansion and contraction by heating and cooling.

In chambers A and B of FIG. 12, donut type baffle plates 1217a and 1217b, disc type baffle plates 1218a and 1218b, and donut type baffle plates 1219a and 1219b, for example, are alternately disposed so as to disperse the heating medium in the lateral direction and reduce the temperature distribution in the lateral direction.

The reaction tubes 1204 may be packed with a catalyst for the purpose of a reaction and enabled to utilize the catalyst as a fixed bed. In the production of acrylic acid by the reaction of two-step catalytic gas phase oxidation of a propylene-containing gas, for example, oxidation catalysts generally used for producing acrolein by the reaction of gas phase oxidation of a raw material gas containing propylene can be used as an upstream catalyst. A downstream catalyst is not particularly restricted, but may include, for example, oxidation catalysts generally used for producing acrylic acid by the gas phase oxidation of a reaction gas mainly containing the acrolein obtained on the upstream by the method for two-step catalytic gas phase oxidation.

The former step catalyst for the production of acrylic acid may be used as the upstream catalyst and the latter step catalyst for the production of acrylic acid as the downstream catalyst.

The catalysts which form the upstream and downstream catalyst beds each do not need to be a unique catalyst. For example, several kinds of catalysts differing in activity may be sequentially packed or such catalysts, when necessary, may be diluted with an inert material such as an inactive carrier. This fact holds true with other catalysts, which will be specifically described herein below.

The catalyst is not specifically restricted on account of the shape, but suitable examples of the shape of catalyst may cite Raschig rings, spheres, cylinders, and rings. As regards the method for forming the catalyst in such a shape, deposition molding, extrusion molding, and tablet molding may be used. The catalyst formed by depositing a catalytic substance on a refractory carrier may be useful.

Before the reaction tubes 1204 are packed with a catalyst, a metallic net or support plate 1214 is set at the lower end of the reaction tubes 1204 for the purpose of preventing the catalyst from falling down. Before the catalyst is set, the reaction tubes 1204, when necessary, are packed with a refractory substance inactive to the reaction and then packed with the upstream catalyst. Then, they are packed with the downstream catalyst. An inactive refractory substance may be interposed between the upstream and downstream catalysts.

FIG. 12 omits the catalysts to permit readily inspection of the drawing. FIG. 13 is a schematic cross section illustrating one example of packing of one reaction tube with the catalyst. As illustrated in FIG. 13, an inactive refractory substance 1322a and an upstream catalyst 1321 are deposited from the lower part of chamber B, an inactive refractory substance 1322b deposited from the upper part of the upstream catalyst through the intermediate tube sheet 1308 to the entrance portion of chamber A, and a downstream catalyst 1323 deposited in the remaining region of chamber A. When the temperature of chamber B is higher than that of chamber A, for example, the raw material gas is partially oxidized by the upstream catalyst 1321, then cooled in the portion of the inactive refractory substance 1322, and thereafter partially oxidized further while maintaining the lowered temperature in the portion of the downstream catalyst 1323 to give a desired product. In the region of chamber A, the portion of the inactive refractory substance 1322 corresponds to a cooling layer and the portion of the downstream catalyst 1323 corresponds to a reaction layer.

Suitable examples of the inactive refractory substance may include α-alumina, alundum, mullite, carborundum, stainless steel, silicon carbide, steatite, earthenware, porcelain, iron, and various sorts of ceramics.

The inactive refractory substance may be in a granular form. The whole layer of an inactive refractory substance is not always required to uniformly pack. For the purpose of effectively cooling the reaction gas, the whole layer of the inactive refractory substance is preferably packed substantially uniformly. This may be applied to other forms than the granular form.

One of the functions of the layer of an inactive refractory substance resides, when the temperature of chamber A is lower than that of chamber B, in adjusting the temperature of the reaction gas to a level in a range proper for the oxidation reaction in the downstream catalyst layer by suddenly cooling the product-containing gas emanating from the upstream catalyst. The layer of the inactive refractory substance is required to dispose in a length enough for the function to be satisfactorily manifested.

In this invention, the layer of inactive refractory substances is disposed in a length sufficient for cooling the reaction gas from the upstream catalyst layer to a temperature proper for the downstream catalyst layer and in a manner such that the catalyst in the outlet part of the upstream catalyst layer and the catalyst in the inlet part of the downstream catalyst layer are both incapable of substantially receiving to the heat influence from the intermediate tube sheet. This invention permits a reduction in the length of layer of the inactive refractory substance because it is capable of alleviating the transfer of the heating medium between the chambers and allaying the heat influence. It is also capable of reducing the length of the reaction tubes packed with the catalysts, namely the length of the reactor.

The layer of the inactive refractory substance is only required to have a length sufficient for cooling the reaction gas entering the downstream catalyst layer from the layer of the inactive refractory substance, namely the reaction gas in the inlet part to the downstream catalyst layer, to a temperature of not more than (the inlet temperature of the heating medium plus 15° C., when the heating medium is advanced in co-current flow to the raw material or produced gas).

Another function of the layer of the inactive refractory substance, through which the reaction gas emanating from the upstream reaction layer passes, resides not only in preventing the substances contained in the reaction gas, i.e. the molybdenum component sublimed from the upstream catalyst and high boiling substances such as terephthalic acid by-produced in the production of acrylic acid, for example, from causing pressure drop but also in preventing these defiling substances from directly entering the downstream catalyst layer and degrading the catalytic property thereof. For the sole sake of this function, it suffices to reduce the void ratio of the inactive refractory substance. If this reduction is unduly large, the excess will be at a disadvantage in aggravating the pressure drop. This invention may set the void ratio of the inactive refractory substance at a level in the range of 40–99.5%, preferably 45–99%. The term "void ratio" used herein is defined by the following formula:

$$\text{Void ratio } (\%) = \{(X-Y)/X\} \times 100$$

wherein X denotes the volume of layer of the inactive refractory substance and Y the real volume of layer of the inactive refractory substance (the term "real volume" means, in the case of a ring, for example, the actual volume minus the central empty part).

If the void ratio is less than 40%, the shortage will enlarge the pressure drop. Conversely, if it exceeds 99.5%, the excess will be at disadvantages in lowering the function of capturing the impurities and degrading the function of cooling the reaction gas as well.

When an inactive refractory substance is inserted in the inlet part to the upstream catalyst for the purpose of preheating the raw material gas, it brings the advantage of increasing the yield of desired products.

In FIG. 12, the raw material gas for a reaction is supplied up-flow to the reactor 1201, exposed therein to the catalyst and allowed to give birth to the desired product, and discharged from the reactor through the upper part thereof. A method for supplying the reaction gas, when necessary, may be varied by altering the sequence of filling the kinds of catalyst so as to supply the reaction gas to the reactor down-flow.

In chamber A, the heating medium discharged through a heating medium outlet port 1212a of an annular conduit 1209a which is disposed on the outer periphery of the shell 1221 and provided with a plurality of openings communicating with the reactor 1201 is cooled by a heat exchanger 1215a. The cooled heating medium is then introduced into chamber A through an annular conduit 1210a which is disposed on the outer periphery of the shell 1221 and provided with a plurality of openings communicating with the reactor 1201 via a heating medium inlet 1211a with a known pump 1216a such as a volute or axial-flow pump. In the reactor 1201, the heating medium enters the shell 1221 from the substantially whole circumference of the peripheral part of the reactor, contacts a bundle of reaction tubes 1204 and meanwhile recovers the heat generated when the reaction is exothermic, advances toward the center of the reactor, and ascends the hole formed in the donut type baffle plate 1219a. The heating medium further advances substantially horizontally along a disc type baffle plate 1218a to contact the bundle of reaction tubes 1204 and meantime recovers the reaction heat, advances toward the substantially whole peripheral part of the reactor, and ascends the outer peripheral part of the disc 1218a. Thereafter, the heating medium, by repeating this process, advances to the annular conduit 1209a disposed on the outer periphery of the reactor 1201. Though a gap may interpose between the donut type baffle plates and the reactor, it is commendable to eliminate this gap for the purpose of reducing the temperature distribution of the heating medium in the reactor.

In chamber B, the heating medium circulates similarly in chamber A.

Then, the method for circulating the heating medium, when necessary, allows the heating medium to be circulated in the reverse direction in either or both chambers A and B. From the viewpoint of protecting the pumps 1216a and b, the heating medium is preferred to pass the pumps 1216a and b after it has passed the heat exchangers 1215a and b and has then acquired a relatively low temperature.

The contents of (I) and (II) above may be suitably combined without departing from the scope of this invention.

Catalyst Used in (I) and (II) Above

In the production of acrylic acid by the reaction of two-step catalytic gas phase oxidation of a propylene-containing gas according to this invention, an oxidation catalyst generally used for producing acrolein by subjecting a propylene-containing raw material gas to a reaction of gas phase oxidation can be used as the upstream catalyst. Similarly, the downstream catalyst is not particularly restricted, but may include, for example, an oxidation catalyst generally used in producing acrylic acid by the gas phase oxidation of a reaction gas which mainly contains the acrolein obtained in the former step by the method of two-step catalytic gas phase oxidation.

Suitable examples of the upstream catalyst may include catalysts represented by the formula, $Mo_a$—$Bi_b$—$Fe_c$—$A_d$—$B_e$—$C_f$—$D_g$—$O_x$, wherein Mo, Bi, and Fe respectively denote molybdenum, bismuth, and iron, A denotes at least one element selected from the group consisting of nickel and cobalt, B denotes at least one element selected from the group consisting of alkali metals and thallium, C denotes at least one element selected from the group consisting of phosphorus, niobium, manganese, cerium, tellurium, tungsten, antimony, and lead, D denotes at least one element selected from the group consisting of silicon, aluminum, zirconium, and titanium, and O denotes oxygen, a, b, c, d, e, f, g, and x respectively denote the atomic ratios of Mo, Bi, Fe, A, B, C, D, and O satisfying the ranges, b=0.1–10, c=0.1–10, d=2–20, e=0.001–5, f=0–5, and g=0–30, on the basis of a=12, and x denotes the numerical value fixed by the states of oxidation of the relevant elements.

Suitable examples of the downstream catalyst may include catalysts represented by the formula, $Mo_a$—$V_b$—$W_c$—$Cu_d$—$A_e$—$B_f$—$C_g$—$O_x$, wherein Mo denotes molybdenum, V vanadium, W tungsten, Cu copper, A at least one element selected from the group consisting of antimony, bismuth, tin, niobium, cobalt, iron, nickel, and chromium, B at least one element selected from the group consisting of alkali metals, alkaline earth metals, and thallium, C at least one element selected from the group consisting of silicon, aluminum, zirconium, and cerium, and O denotes oxygen, a, b, c, d, e, f, g, and x respectively denote the atomic ratios of Mo, V, W, Cu, A, B, C, and O satisfying the ranges, b=2–14, c=0–12, d=0.1–5, e=0–5, f=0–5, and g=0–20, on the basis of a=12, and x denotes the numerical value fixed by the states of oxidation of the relevant elements.

As the catalyst to be used in producing methacrylic acid by the reaction of two-step catalytic gas phase oxidation of isobutylene, t-butanol, or methyl-t-butyl ether according to this invention, an oxidation catalyst generally used as the upstream catalyst in producing methacrolein by the reaction of gas phase oxidation of a raw material gas containing isobutylene, for example, can be used. The downstream catalyst is not particular restricted, but may include an oxidation catalyst generally used in producing methacrylic acid by the gas phase oxidation of a reaction gas mainly containing the methacrolein obtained by the former step of the method for two-step catalytic gas phase oxidation.

Suitable examples of the upstream catalyst may include catalysts of the formula, $Mo_a$—$W_b$—$Bi_c$—$Fe_d$—$A_e$—$B_f$—$C_g$—$D_h$—$O_x$, wherein Mo, W, and Bi respectively denote molybdenum, tungsten, and bismuth, Fe denotes iron, A denotes nickel and/or cobalt, B denotes at least one element selected from the group consisting of alkali metals, alkaline earth metals, and thallium, C denotes at least one element selected from the group consisting of phosphorus, tellurium, antimony, tin, cerium, lead, niobium, manganese, and zinc, D denotes at least one element selected from the group consisting of silicon, aluminum, titanium, and zirconium, and O denotes oxygen, a, b, c, d, e, f, g, h, and x respectively denote the atomic ratios of Mo, W, Bi, Fe, A, B, C, D, and O satisfying the ranges, b=0–10, c=0.1–10, d=0.1–20, e=2–20, f=0.001–10, g=0–4, and h=0–30 on the basis of a=12, and x denotes the numerical value fixed by the states of oxidation of the relevant elements.

The downstream catalyst is not particularly restricted but may comprise at least one oxide catalyst containing molybdenum and phosphorus as main components. For example, phosphomolybdic acid type heteropoly acids and metal salts thereof prove advantageous. Suitable examples of the downstream catalyst may include catalysts of the formula, $Mo_a$—$P_b$—$A_c$—$B_d$—$C_e$—$D_f$—$O_x$, wherein Mo denotes molybdenum, P denotes phosphorus, A denotes at least one element selected from the group consisting of arsenic, antimony, germanium, bismuth, zirconium, and selenium, B denotes at least one element selected from the group consisting of copper, iron, chromium, nickel, manganese, cobalt, tin, silver, zinc, palladium, rhodium, and tellurium, C denotes at least one element selected from the group consisting of vanadium, tungsten, and niobium, D denotes at least one element selected from the group consisting of alkali metals, alkaline earth metals, and thallium, and O denotes oxygen, a, b, c, d, e, f, and x respectively denote the atomic ratios of Mo, P, A, B, C, D, and O satisfying the ranges, b=0.5–4, c=0–5, d=0–3, e=0–4, and f=0.01–4 on the basis of a=12, and x denotes the numerical value fixed by the states of oxidation of the relevant elements.

The catalyst is not particularly discriminated on account of shape, but may be in the shape of spheres, circular columns, or cylinders. Suitable methods for forming the catalyst in such a shape may include forming on a carrier, extrusion molding, and tablet molding. The catalyst obtained by depositing a catalytic substance on a refractory carrier is also useful.

Reaction Conditions to be Used in (I) and (II) Above

Conditions for the reaction of a gas phase catalytic oxidation of propylene or isobutylene with molecular oxygen may be set by a known method. In the case of propylene, for example, the propylene concentration in the raw material gas is in the range of 3–15 vol. %, the ratio of molecular oxygen to the propylene in the range of 1–3, and the remainder comprises nitrogen, steam, carbon oxides, propane, etc.

Air is advantageously used as the feed source for molecular oxygen. An oxygen-enriched air and pure oxygen, when necessary, may be used instead. The supply of such source for molecular oxygen is implemented by the one-pass or recycling method. Preferably, the reaction temperature is in the range of 250° C.–450° C., the reaction pressure in the range of normal pressure to 5 atmospheres, and the space velocity in the range of 500–3000 h$^{-1}$ (STP).

In the case of gas phase catalytic oxidation of isobutylene, the isobutylene concentration in the raw material gas is in the range of 1–10 vol. %, the concentration of molecular oxygen 3–20 vol. % and the concentration of steam 0–60 vol. % respectively relative to isobutylene, and the remainder comprises nitrogen, steam, carbon oxides, etc. Air is advantageously used as the feed source for molecular oxygen. An oxygen-enriched air and pure oxygen, when necessary, are also usable. Preferably, the reaction temperature is in the range of 250–450° C., the reaction pressure in the range of normal pressure to five atmospheres, and the spatial velocity in the range of 300–5000 h$^{-1}$ (STP).

Then, the production of acrylic acid is effected by packing the bundled reaction tubes in the shell of the heat exchanger type second shell-and-tube reactor with the oxidation catalyst (downstream catalyst), feeding into the reactor the mixed gas prepared by adding secondary air, secondary oxygen, or steam, when necessary, to the acrolein-containing gas obtained by the former-step reaction at a reaction temperature (the temperature of the catalyst in the reactor) of 100–380° C., preferably 150–350° C., at a spatial velocity of 300–5,000 hr$^{-1}$ (STP), and performing the latter-step reaction.

The production of methacrylic acid is effected by packing the bundled reaction tubes in the shell of the heat exchanger type second shell-and-tube reactor with the oxidation catalyst (downstream catalyst) containing molybdenum and phosphorus, feeding into the reactor the mixed gas prepared by adding secondary air, secondary oxygen, or steam, when necessary, to the methacrolein-containing gas obtained by the former-step reaction at a reaction temperature (the temperature of the catalyst in the reactor) of 100–380° C., preferably 150–350° C., at a spatial velocity of 300–5,000 hr$^{-1}$ (STP), and carrying out the latter-step reaction.

By use of the present reactor, maleic anhydride can be produced in a known reaction system with a known catalyst by using a benzene- or butane-containing gas as the raw material, and phthalic anhydride can be also produced in a known reaction system with a known catalyst by using a xylene- and/or naphthalene-containing gas as the raw material.

The reactor constructed as described above is suitable for the production, by the reaction of catalytic gas phase oxidation, of acrolein from propylene; methacrolein from at least one member selected from the group consisting of isobutylene, t-butanol, and methyl-t-butyl ether; maleic anhydride from benzene; maleic anhydride from butane; phthalic anhydride from xylene and/or naphthalene; acrylic acid from acrolein; and methacrylic acid from methacrolein, particularly for the production of (meth)acrolein from (meth)acrylic acid and/or (meth)acrolein.

EXAMPLES

Now, this invention will be described more specifically, but not restricted below with reference to examples.

Referential Example 1, Production of Catalyst

In 150 liters of purified water kept heated and stirred, 100 kg of ammonium molybdate and 6.3 kg of ammonium paratungstate were dissolved. To the resultant solution, an aqueous nitrate solution prepared by mixing a solution of 68.7 kg of cobalt nitrate in 100 liters of purified water, a solution of 19 kg of ferric nitrate in 30 liters of purified water, and a solution of 22.9 kg of bismuth nitrate in 30 liters of purified water incorporating therein 6 liters of concentrated nitric acid was added dropwise. Then, a solution of 14.2 kg of an aqueous 20 wt. % silica sol solution and 0.29 kg of potassium nitrate in 15 liters of purified water was added. The suspension thus obtained was heated and stirred till vaporization to dryness and then dried and pulverized. The produced powder was molded into cylinders 5 mm in diameter and calcined as swept with air at 460° C. for six hours to afford a catalyst. The produced catalyst had this composition: Mo 12, Bi 1, Fe 1, Co 5, W 0.5, Si 1, and K 0.06.

Referential Example 2, Production of Catalyst

In 150 liters of purified water kept heated and stirred, 100 kg of ammonium molybdate, 6.3 kg of ammonium paratungstate, and 27.5 kg of nickel nitrate were dissolved. To the resultant solution, an aqueous nitrate solution prepared by mixing a solution of 68.7 kg of cobalt nitrate in 100 liters of purified water, a solution of 19 kg of ferric nitrate in 30 liters of purified water, and a solution of 22.9 kg of bismuth nitrate in 30 liters of purified water incorporating therein 6 liters of concentrated nitric acid was added dropwise. Then, a solution of 14.2 kg of an aqueous 20 wt. % silica sol solution and 0.38 kg of potassium nitrate in 15 liters of purified water was added. The suspension thus obtained was heated and stirred till vaporization to dryness and then dried and pulverized. The produced powder was molded into cylinders 5 mm in diameter and calcined as swept with air at 460° C. for six hours to afford a catalyst. The produced catalyst had this molar composition: Mo 12, Bi 1.0, Fe 1.0, Co 5, Ni 2.0, W 0.5, Si 1.0, and K 0.08.

Referential Example 3, Production of Catalyst

In 500 liters of purified water kept heated and stirred, 100 kg of ammonium molybdate, 19.1 kg of ammonium paratungstate, and 30.4 kg of ammonium metavanadate were dissolved. To the resultant solution, a solution of 20.5 kg of copper nitrate and 3.4 kg of antimony trioxide in 50 liters of purified water was added. The mixed solution and 350 kg of a silica-alumina carrier having an average particle diameter of 5 mm added thereto were evaporated together to dryness to deposit a catalyst component on the carrier. The carried catalyst component was calcined at 400° C. for six hours to afford a catalyst. The catalyst in a required amount was obtained by repeating this process. This catalyst had this molar composition: Mo 12, V 5.5, W 1.5, Cu 1.8 and Sb 0.5.

Referential Example 4, Production of Catalyst

In 500 liters of purified water kept heated and stirred, 100 kg of ammonium molybdate, 12.7 kg of ammonium paratungstate, and 27.6 kg of ammonium metavanadate were dissolved. To the resultant solution, a solution of 25 kg of copper nitrate and 1.4 kg of antimony trioxide in 50 liters of purified water were added. This mixed solution and 350 kg of a silica-alumina carrier having an average particle diameter of 5 mm were evaporated together to dryness to have a catalytic component deposited on the carrier and then calcined at 400° C. for six hours to afford a catalyst. The catalyst in a required amount was obtained by repeating this process. This catalyst had this molar composition: Mo 12, V 5, W 1, Cu 2.2, Sb 0.2.

Referential Example 5, Production of Catalyst

In 150 liters of purified water kept heated and stirred, 100 kg of ammonium molybdate and 6.3 kg of ammonium paratungstate were dissolved. To this solution, an aqueous nitrate solution prepared by mixing a solution of 68.7 kg of cobalt nitrate in 100 liters of purified water, a solution of 22.9 kg of ferric nitrate in 30 liters of purified water, and a solution of 27.5 kg of bismuth nitrate in 30 liters of purified water incorporating therein 6 liters of concentrated nitric acid was added dropwise. Then, a solution of 14.2 kg of an aqueous 20 wet. % silica sol solution and 0.29 g kg of potassium nitrate in 15 liters of purified water was added thereto. The suspension thus obtained was heated and stirred till vaporization to dryness and then dried and pulverized. The produced powder was molded into cylinders 5 mm in diameter and calcined at 460° C. for six hours as swept with air to afford a catalyst. This catalyst in a required amount was obtained by repeating this process. This catalyst had this molar composition, Mo 12, Bi 1.2, Fe 1.2, Co 5, W 0.5, Si 1, K 0.06.

Example I-1

With the reactor illustrated in FIG. 3, the reaction tubes were packed with 5.6 m³ of a catalyst obtained in REFERENTIAL EXAMPLE 1 of production of catalyst for forming acrolein mainly from propylene and then the raw material gas composed of 7 vol. % of propylene, 12.6 vol. % of oxygen, 10 vol. % of steam, and 70.4 vol. % of nitrogen, etc. was introduced into the reaction tubes at a flow rate such that the contact time thereof with the catalyst was 2 seconds. A heating medium composed of 50 wet. % of potassium nitrate and 50 wet. % of sodium nitrite was circulated at an inlet temperature of 315° C. with an axial-flow pump operated at 2900 m³/h. In the reactor, reaction tubes not supported by donut type baffle plates and reaction tubes not supported by disc type baffle plates were present.

When the product emanating from the product discharge port of the reactor was analyzed, the conversion of propylene was found to be 97.0% and the selectivity to acrolein to be 84.8%.

Comparative Example I-1

A reaction is performed by following the procedure of Example I-1 while changing the diameter of hole in the donut type baffle plate to the diameter shown in Table 1. The results are shown in Table 1. It is noted from the results that the rate of selectivity and the yield are not changed and the power for the axial-flow pump is increased to 5.4 times the power used in Example I-1. In the reactor, reaction tubes not supported by the donut type baffle plates are absent and reaction tubes not supported by the disc type baffle plates are present.

Comparative Example I-2

In a reactor destitute of reaction tubes not supported by donut type baffle plates, acrolein is obtained by following the procedure of Example I-1 while changing the diameters of central empty spaces and holes in the donut type baffle plates to those shown in Table 1. The results are shown in Table 1. In the reactor, reaction tubes not supported by the donut type baffle plates are not present and reaction tubes not supported by the disc type baffle plates are present. It is noted from the results that the rate of selectivity and yield are not changed and the power for the axial-flow pump is increased to 1.8 times the power used in Example I-1.

Example I-2

Acrolein is obtained by following the procedure of Example I-1 while using the same diameters for the donut type baffle plates and the central empty space as in Example I-1 and changing the diameters of the disc type baffle plates and the reactor shell to those shown in Table 1. In the reactor, reaction tubes not supported by the donut type baffle plates are present and reaction tubes not supported by the disc type baffle plates are absent. The ratio of the power for the axial-flow pump is 0.97.

Comparative Example I-3

Acrolein is obtained by following the procedure of Example I-2 while changing the diameter of the holes in the donut type baffle plates to the diameter shown in Table 1. The results are shown in Table 1. In the reactor, reaction tubes not supported by the donut type baffle plates and reaction tubes not supported by the disc type baffle plates are absent.

Example I-3

Acrylic acid was obtained by using a single reactor identical with the reactor of Example I-1 in shell diameter of the reactor, diameter of the central empty space, diameter of the disc type baffle plate, diameter of holes in the donut type baffle plates, ratio of area of the central empty space/area of the shell, ratio of area of the disc type plate/area of the shell, and ratio of area of the holes in the donut type baffle plates/area of the shell except that as shown in FIG. 12, 4100 reaction tubes of steel 7 m in length, 25 mm in inside diameter, and 29 mm in outside diameter were used, an intermediate tube sheet was adopted, 5.6 m³ of Referential Example 2 of production of catalyst as the upstream catalyst and 7.0 m³ of the catalyst of Referential Example 3 of production of catalyst as the downstream catalyst were filed, and the heating medium at 315° C. and 2900 m³/h in the upstream step and at 280° C. and 2000 m³/h in the downstream step was circulated. The results are shown in Table 1.

When the product emanating from the product discharge port of the reactor was analyzed, the conversion of propylene was found to be 97.6% and the selectivity to acrylic acid to be 90.1%.

Comparative Example I-4

Acrylic acid is obtained by following the procedure of Example I-3 while changing the diameter of shell of the reactor, the diameter of the disc type baffle plates, and the diameter of holes of the donut type baffle plates to the diameters shown in Table 1. The results are shown in Table 1. In the reactor, reaction tubes not supported by the donut type baffle plates and reaction tubes not supported by the disc type baffle plates are absent.

TABLE 1

|  | Ex. I-1 | Ex. I-2 | Com. Ex. I-1 | Com. Ex. I-2 | Com. Ex. I-3 | Ex. I-3 | Single Reactor Com. Ex. I-4 |
|---|---|---|---|---|---|---|---|
| (A) (mm) | 2700 | 3000 | 2700 | 2750 | 3000 | 2700 | 3000 |
| (B) (mm) | 300 | 300 | 300 | 500 | 300 | 300 | 300 |
| (C) (mm) | 2400 | 2700 | 2400 | 2400 | 2700 | 2400 | 2700 |
| (D) (mm) | 1100 | 1100 | 300 | 500 | 300 | 1100 | 300 |
| (E) | 1.23 | 1.00 | 1.23 | 3.31 | 1.00 | 1.23 | 1.00 |
| (F) | 79.0 | 81.0 | 79.0 | 76.2 | 81.0 | 79.0 | 81.0 |
| (G) | 16.6 | 13.4 | 1.23 | 3.31 | 1.00 | 16.6 | 1.00 |
| (H) (mm) | 3250 | 3250 | 3250 | 3250 | 3250 | 7000 | 7000 |
| (I) | 4100 | 4100 | 4100 | 4100 | 4100 | 4100 | 4100 |
| (J) (mm) | 29 | 29 | 29 | 29 | 29 | 29 | 29 |
| (K) (mm) | 25 | 25 | 25 | 25 | 25 | 25 | 25 |
| (L) (mm) | 38 | 38 | 38 | 38 | 38 | 38 | 38 |
| (M) | 1.00 | 1.23 | 1.00 | 1.04 | 1.23 | 1.00 | 1.23 |
| (N) (1st) (kW) | 83 | 80 | 450 | 152 | 446 | 83 | 446 |
| (O) (1st) | 1.0 | 0.97 | 5.4 | 1.8 | 5.4 | 1.0 | 5.4 |
| (P) (2nd) (kW) |  |  |  |  |  | 60 | 131 |
| (Q) (2nd) |  |  |  |  |  | 1.0 | 2.2 |
| (R) (%) | 97.0 | 97.3 | 96.9 | 96.9 | 97.0 | 97.6 | 97.3 |
| (S) (%) | 84.8 | 84.4 | 84.9 | 84.9 | 84.9 | 90.1 | 90.5 | wherein
- (A): Shell diameter of reactor
- (B): Diameter of central empty space part
- (C): Diameter of disc type baffle plate
- (D): Diameter of holes of donut type baffle plate
- (E): Area of central empty space/area of shell
- (F): Area of disc type plate/area of shell
- (G): Area of hole of donut type baffle plate/area of shell
- (H): Length of reaction tube
- (I): Number of reaction tubes
- (J): Outside diameter of reaction tube
- (K): Inside diameter of reaction tube
- (L): Pitch of reaction tubes
- (M): Ratio of shell area
- (N)): Power for axial-flow pump
- (O): Ratio of power for axial-flow pump
- (Q): Power for axial-flow pump
- (P): Ratio of power for axial-flow pump
- (R): Conversion of propylene
- (S): Selectivity of acrolein Example II-1

FIGS. 8 and 9 are diagrams illustrating the reactor as one mode of embodying this invention. The characteristic properties of this reactor are shown in Table 2 below. The numbers of reaction tubes in three regions of reaction tubes were 2123, 2123, and 2123, involving no difference (0%). The cross-sectional area of the circulation passage was 2.4% relative to the cross-sectional area of the reactor {Formula= 100×[((3400−500)/2) (50) (3)]/($\pi$/4·(3400)$^2$)}.

The reaction tubes were packed with 9.4 m$^3$ of a catalyst for producing acrylic acid mainly from acrolein, and the raw material gas composed of 5 vol. % of acrolein, 5 vol. % of oxygen, 17 vol. % of steam, and 73 vol. % of nitrogen, etc. was introduced into the tubes at a ratio such that the contact time with the catalyst was 2.5 seconds. The catalyst used herein was prepared by Referential Example 4 of production of catalyst.

A heating medium composed of 50 wt. % of potassium nitrate and 50 wt. % of sodium nitrite was circulated at an inlet temperature of 270° C. with an axial-flow pump operating at 2700 m$^3$/h in the shell. The number of openings was 50 each in the upper and lower annular conduits. The conditions involved herein were T1=220° C., T2=270° C., W1=81 m$^3$/h, and W2=2700 m$^3$/h.

The maximum temperature difference in the horizontal direction of the heating medium at a fixed height was 2° C. As a result, the conversion of acrolein was 99.2% and the selectivity to acrylic acid was 95.1%.

TABLE 2

|  | Ex. II-1 | Com. Ex.II-1 |
|---|---|---|
| Length/pitch of reaction tube*) (mm) | 3500/38 | ← |
| Inside diameter/outside diameter of reaction tube (mm) | 25/29 | ← |
| Number of reaction tubes | 6369 | ← |
| Shell diameter of reactor (mm) | 3400 | ← |
| Diameter of central empty area (mm) | 500 | ← |
| Diameter of donut type baffle plate (mm) | 500 | ← |
| Diameter of disc type baffle plate (mm) | 3000 | ← |
| Number of circulation passages | 3 | 0 |
| Width of circulation passage (mm) | 50 | 0 |

*)Configuration in equilateral triangle

Comparative Example II-1

The same reactor was operated under the same conditions as in Example II-1 except that no circulation passage was formed in the reactor. The maximum temperature difference in the horizontal direction of the heating medium at a fixed height was 5° C.

As a result, the conversion of acolein was 99.0% and the selectivity to acrylic acid 92.8%.

Example II-2

Synthesis of acrylic acid by the oxidation of propylene was implemented by using a vertical shell-and-tube containing 6369 reaction tubes of steel 6500 mm in length, 25 mm in inside diameter, and 29 mm in outside diameter as shown in FIG. 12 and having an intermediate tube sheet and introducing a raw material gas composed of 7.0 vol. % of proplylene, 12.6 vol. % of oxygen, 10.0 vol. % of steam, and 70.4 vol. % of inert gas comprising nitrogen etc. into the reaction tubes packed with 7.5 m³ of the catalyst of Referential Example 5 as the upstream catalyst and 9.4 m³ of the catalyst of Referential Example 4 as the downstream catalyst.

The characteristic properties of the reactor are shown in Table 3 below. The numbers of reaction tubes in three regions of reaction tubes were respectively 2123, 2123, and 2123, involving no difference in the reaction tubes. The cross-sectional area of the circulation passage was 2.4% relative to the cross-sectional area of the reactor {Formula= 100×[((3400−500)/2) (50) (5)]/(π/4·(3400)²)}.

In chamber A (downstream side), a heating medium composed of 50 wt. % of potassium nitrate and 50 wt. % of sodium nitrite was circulated upward at an inlet temperature of 270° C. with an axial-flow pump operated at 2700 m³/h. The number of openings was 50 each in the upper and lower annular conduits. The conditions used herein were T1=220° C., T2=270° C., W1=97 m³/h, and W2=2700 m³/h.

In chamber B (upstream side), a heating medium composed of 50 wt. % of potassium nitrate and 50 wt. % of sodium nitrite was circulated upward at an inlet temperature of 315° C. with an axial-flow pump operated at 3800 m³/h. The number of openings was 50 each in the upper and lower annular conduits. The conditions in this case were T1=220° C., T2=305° C., W1=48 m³/h, and W2=3800 m³/h.

The maximum temperature difference in the horizontal direction of the heating medium at a fixed height was 2° C. As a result, the conversion of propylene was 97.3% and the selectivity to acrylic acid 90.5%.

TABLE 3

|  | Ex. II-2 | Com. ExII-2 |
| --- | --- | --- |
| Length/pitch of reaction tube*) (mm) | 6500/36 | ← |
| Inside diameter/outside diameter of reaction tube (mm) | 25/29 | ← |
| Number of reaction tubes | 6369 | ← |
| Shell diameter of reactor (mm) | 3400 | ← |
| Diameter of central empty area (mm) | 500 | ← |
| Hole diameter of donut type baffle plate (mm) | 300 | ← |
| Diameter of disc type baffle plate (mm) | 3000 | ← |
| Number of circulation passages | 3 | 0 |
| Width of circulation passage (mm) | 50 | 0 |

*)Configuration in equilateral triangle

Comparative Example II-2

The same reactor was operated under the same conditions as in Example II-2 except that the reactor was devoid of a circulation passage.

The maximum temperature difference in the horizontal direction of the heating medium at a fixed height was 5° C.

As a result, the conversion of propylene was 97.1% and the selectivity to acrylic acid 89.0%.

The entire disclosure of Japanese Patent Application Nos. 11-246057 and 11-246058 filed on Aug. 31, 1999 including specification, claims, drawings and summary are incorporated herein by reference in its entirety.

What is claimed is:

1. A shell-and-tube type reactor, comprising: a cylindrical shell having disposed on the periphery thereof a plurality of annular conduits for guiding a heating medium in or out in the radial direction and having a raw material inlet and a product outlet;

a circulation device for mutually connecting a plurality of annular conduits;

a plurality of reaction tubes constrained to the reactor by a plurality of tube sheets;

donut type baffle plates and disc type baffle plates disposed in the longitudinal direction of the reaction tubes and adapted to vary the direction of the heating medium introduced into the shell;

said reaction tubes being restrained at center distances 1.2–1.4 times the outside diameter of the reaction tube;

an empty space devoid of a configuration of the reaction tubes at a center of the shell;

said reaction tubes unsupported by the donut type baffle plate in the center hole side; and a gas discharge conduit discharging a gas accumulated in the shell.

2. A reactor according to claim 1 further comprising reaction tubes not supported by the disc type baffle plates.

3. A reactor according to claim 1, wherein a cross sectional area of the empty space is in the range of 0.5–5% of the cross sectional area of the shell, a cross sectional area of the disc type baffle plates in the range of 50–95% of the cross sectional area of the shell, and a cross sectional area of holes in the donut type baffle plates in the range of 2–25% of the cross sectional area of the shell.

4. A reactor according to claim 1, further comprising at least one circulation passage for the heating medium between an empty space devoid of a configuration of reaction tubes in the center of the shell and the peripheral part of the shell; and the circulation passage has no reaction tubes between them.

5. A reactor according to claim 2, wherein a cross sectional area of the empty space is in the range of 0.5–5% of the cross sectional area of the shell, a cross sectional area of the disc type baffle plates in the range of 50–95% of the cross sectional area of the shell, and a cross sectional area of holes in the donut type baffle plates in the range of 2–25% of the cross sectional area of the shell.

6. A reactor according to claim 3, wherein a value calculated by |(Number of reaction tubes in individual regions)/(average number of reaction tubes in the regions)− 1|×100 is within 3%.

7. A reactor according to claim 4, wherein a value calculated by |(Number of reaction tubes in individual regions)/(average number of reaction tubes in the regions)− 1|×100 is within 3%.

8. A reactor according to claim 4, wherein a cross-sectional area of the circulation passage is in the range of 0.5–5% based on the cross-sectional area of the shell.

9. A reactor according to claim 5, further comprising at least one circulation passage for the heating medium between an empty space devoid of a configuration of reaction tubes in the center of the shell and the peripheral part of the shell.

10. A reactor according to claim 7, wherein a cross sectional area of the empty space is in the range of 0.5–5% of the cross sectional area of the shell, a cross sectional area of the disc type baffle plates in the range of 50–95% of the cross sectional area of the reactor, and a cross sectional area of holes in the donut type baffle plates in the range of 2–25% of the cross sectional area of the shell.

11. A reactor according to claim 1 further comprising at least two of circulation conduits for supplying or withdrawing the heating medium to or from the shell.

12. A shell-and-tube type reactor comprising:

a cylindrical shell having disposed on the periphery thereof a plurality of annular conduits for guiding a heating medium in or out in the radial direction and having a raw material inlet and a product outlet;

a circulation device for mutually connecting a plurality of annular conduits;

a plurality of reaction tubes constrained to the reactor by a plurality of tube sheets;

donut type baffle plates and disc type baffle plates disposed in the longitudinal direction of the reaction tubes and adapted to vary the direction of the heating medium introduced into the shell;

said reaction tubes being restrained at center distances 1.2–1.4 times the outside diameter of the reaction tube;

an empty space devoid of a configuration of the reaction tubes at a center of the shell;

said reaction tubes unsupported by the donut type baffle plate in the center hole side; and a plurality of opening rows for allowing the heating medium to pass, an width B of the opening being in the range of 5 to 50% based on the center distance, and a ration of opening length C/opening width B being in the range of 0.2 to 20.

13. A reactor according to claim 12, wherein at least one of the opening rows has more than 2 openings.

14. A reactor according to claim 1 further comprising two chambers along with the direction of a raw material gas inlet to a product outlet, said chamber is partitioned with a tube sheet.

15. A reactor according to claim 14, further comprising at least one circulation passage for the heating medium between an empty space devoid of a configuration of reaction tubes in the center of the shell and the peripheral part of the shell.

16. A reactor according to claim 14, wherein a cross sectional area of the empty space is in the range of 0.5–5% of the cross sectional area of the shell, a cross sectional area of the disc type baffle plates in the range of 50–95% of the cross sectional area of the reactor, and a cross sectional area of holes in the donut type baffle plates in the range of 2–25% of the cross sectional area of the shell.

17. A reactor according to claim 15, wherein a value calculated by |(Number of reaction tubes in individual regions)/(average number of reaction tubes in the regions)−1|×100 is within 3%.

18. A method for the production of (meth)acrylic acid and/or (meth)acrolein by means of catalytic gas phase oxidation using a reactor set forth in claim 1.

* * * * *